(12) United States Patent
Johnson et al.

(10) Patent No.: US 11,828,685 B2
(45) Date of Patent: Nov. 28, 2023

(54) SYNTACTIC FOAMS AS MECHANICALLY-TRIGGERED CAPTURE VEHICLES

(71) Applicant: Research Triangle Institute, Research Triangle Park, NC (US)

(72) Inventors: Leah Marie Johnson, Durham, NC (US); Nicolas Daniel Huffman, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 291 days.

(21) Appl. No.: 17/184,887

(22) Filed: Feb. 25, 2021

(65) Prior Publication Data

US 2021/0262904 A1    Aug. 26, 2021

Related U.S. Application Data

(60) Provisional application No. 62/981,116, filed on Feb. 25, 2020.

(51) Int. Cl.
  *G01N 1/10* (2006.01)
  *C08J 9/32* (2006.01)
  (Continued)

(52) U.S. Cl.
  CPC ............ *G01N 1/10* (2013.01); *C08J 9/32* (2013.01); *C08K 7/28* (2013.01); *G01N 33/1886* (2013.01);
  (Continued)

(58) Field of Classification Search
  None
  See application file for complete search history.

(56) References Cited

U.S. PATENT DOCUMENTS

| | | | |
|---|---|---|---|
| 3,242,740 A * | 3/1966 | Niskin | G01N 1/16 374/102 |
| 3,563,096 A * | 2/1971 | Kinkelaar | G01N 1/12 73/864.32 |

(Continued)

FOREIGN PATENT DOCUMENTS

| | | | |
|---|---|---|---|
| CN | 105417617 B * | 5/2018 | C02F 1/285 |

OTHER PUBLICATIONS

N. Gupta, S.E. Zeltmann, V.C. Shunmugasamy, D. Pinisetty, Applications of Polymer Matrix Syntactic Foams, JOM 66(2) (2014) 245-254.

(Continued)

*Primary Examiner* — Daniel S Larkin
(74) *Attorney, Agent, or Firm* — Stanek Lemon Crouse & Meeks, PA

(57) ABSTRACT

Syntactic foams are materials including hollow microspheres distributed throughout a cured polymeric resin. Hollow microspheres within syntactic foams, including collapsible shells that enclose empty cavities, can serve as receptacles to capture environmental constituents upon applied temperature and pressure. An epoxy formulation including of EPON™ 828, HELOXY™ 61, and TETA was combined with hollow glass microspheres with isostatic crush strengths of 300, 3000, and 10,000 psi. Effects of pressure and temperature on the mechanical properties were evaluated via dynamic mechanical analysis. Storage modulus and glass transition temperature depended on formulation. Upon exposure to specific temperature and pressures, the hollow glass spheres embedded within the resin lose mechanical integrity and collapse, resulting in the generation of unencapsulated void spaces, primed to capture embedded liquid. Controllable loss of mechanical integrity enables syntactic foams to serve as on-demand receptacles (Continued)

SYNTACTIC FOAM MATERIAL CONTAINS HOLLOW GLASS SPHERES

HEAT

PRESSURE

AN ENVIRONMENTAL SAMPLE IS COLLECTED WITHIN THE FRACTURED SPHERES AND THE CONTENT IS ANALYZED to retain constituents in the surrounding environment, resulting from externally triggered pressures and temperatures.

18 Claims, 10 Drawing Sheets

(51) Int. Cl.
  C08K 7/28    (2006.01)
  G01N 33/18   (2006.01)
  G01N 33/28   (2006.01)

(52) U.S. Cl.
  CPC ...... *G01N 33/2858* (2013.01); *C08J 2363/00* (2013.01)

(56) References Cited

U.S. PATENT DOCUMENTS

| | | | | |
|---|---|---|---|---|
| 3,610,037 | A * | 10/1971 | Greene | G01N 1/10 73/863.23 |
| 3,715,913 | A * | 2/1973 | Anderson | G01N 1/10 73/864.31 |
| 4,157,664 | A * | 6/1979 | Robinson | G01N 1/12 73/864.66 |
| 4,271,704 | A * | 6/1981 | Peters | G01N 1/12 166/264 |
| 5,869,173 | A * | 2/1999 | Zheng | C08K 7/28 428/313.5 |
| 9,493,643 | B2 * | 11/2016 | Li | C08L 25/08 |
| 2014/0303287 | A1 * | 10/2014 | Li | C08G 18/664 427/407.1 |

OTHER PUBLICATIONS

N.D. Gallo, C. James, H. Kevin, F. Patricia, H.B. Douglas, A.L. Lisa, Submersible- and lander-observed community patterns in the Mariana and New Britain trenches: Influence of productivity and depth on epibenthic and scavenging communities, Deep Sea Research Part I: Oceanographic Research Papers 99(Supplement C) (2015) 119-133.
L. Watkins, E. Hershey, Syntactic foam improves deepwater flowline thermal insulation, Oil & Gas Journal, PennWell Corporation, Tulsa, 2001, pp. 49-54.
X. Lefebvre, Sauvant-Moynot, D. Choqueuse, P. Chauchot, Durability of Syntactic Foams for Deep Offshore Insulation: Modelling of Water Uptake under Representative Ageing Conditions in Order to Predict the Evolution of Buoyancy and Thermal Conductivity, Oil & Gas Science and Technology—Rev. IFP 64(2) (2009) 165-178.
A.J. Hodge, Kaul, R.K., McMahon, W.M., Sandwich Composite, Syntactic Foam Core Based, Application for Space Structures, 45th SAMPE Symposium, Long Beach, CA; United States, 2000.
Advanced Materials: Adhesives, syntactics and laminating solutions for high performance, Huntsman Corporation, 2012.
P.K. Rohatgi, D. Weiss, N. Gupta, Applications of fly ash in synthesizing low-cost MMCs for automotive and other applications, JOM 58(11) (2006) 71-76.
L. Zhang, J. Ma, Effect of coupling agent on mechanical properties of hollow carbon microsphere/phenolic resin syntactic foam, Composites Science and Technology 70(8) (2010) 1265-1271.
S.T. Benton, C.R. Schmitt, Preparation of syntactic carbon foam, Carbon 10(2) (1972) 185-190.
N. Gupta, R. Ye, M. Porfiri, Comparison of tensile and compressive characteristics of vinyl ester/glass microballoon syntactic foams, Composites Part B: Engineering 41(3) (2010) 236-245.
C. Swetha, R. Kumar, Quasi-static uni-axial compression behaviour of hollow glass microspheres/epoxy based syntactic foams, Materials & Design 32(8) (2011) 4152-4163.
X.F. Tao, L.P. Zhang, Y.Y. Zhao, Al matrix syntactic foam fabricated with bimodal ceramic microspheres, Materials & Design 30(7) (2009) 2732-2736.
D.K. Balch, D.C. Dunand, Load partitioning in aluminum syntactic foams containing ceramic microspheres, Acta Materialia 54(6) (2006) 1501-1511.
G. Nikhil, N. Ruslan, Tensile properties of glass microballoon-epoxy resin syntactic foams, Journal of Applied Polymer Science 102(2) (2006) 1254-1261.
B. Song, W. Chen, D.J. Frew, Dynamic Compressive Response and Failure Behavior of an Epoxy Syntactic Foam, Journal of Composite Materials 38(11) (2004) 915-936.
K. Okuno, R.T. Woodhams, Mechanical Properties and Characterization of Phenolic Resin Syntactic Foams, Journal of Cellular Plastics 10(5) (1974) 237-244.
D.U. Shah, F. Vollrath, D. Porter, Silk cocoons as natural macroballoon fillers in novel polyurethane-based syntactic foams, Polymer 56 (2015) 93-101.
M. Koopman, K.K. Chawla, K.B. Carlisle, G.M. Gladysz, Microstructural failure modes in three-phase glass syntactic foams, J Mater Sci 41(13) (2006) 4009-4014.
B. John, C.P.R. Nair, K.A. Devi, K.N. Ninan, Effect of low-density filler on mechanical properties of syntactic foams of cyanate ester, J Mater Sci 42(14) (2007) 5398-5405.
H.S. Kim, P. Plubrai, Manufacturing and failure mechanisms of syntactic foam under compression☆, Composites Part A: Applied Science and Manufacturing 35(9) (2004) 1009-1015.
L. Bardella, G. Perini, A. Panteghini, N. Tessier, N. Gupta, M. Porfiri, Failure of glass-microballoons/thermoset-matrix syntactic foams subject to hydrostatic loading, European Journal of Mechanics—A/Solids 70 (2018) 58-74.
N. Gupta, E. Woldesenbet, P. Mensah, Compression properties of syntactic foams: effect of cenosphere radius ratio and specimen aspect ratio, Composites Part A: Applied Science and Manufacturing 35(1) (2004) 103-111.
E. Rizzi, E. Papa, A. Corigliano, Mechanical behavior of a syntactic foam: experiments and modeling, International Journal of Solids and Structures 37(40) (2000) 5773-5794.
L. Bardella, F. Malanca, P. Ponzo, A. Panteghini, M. Porfiri, A micromechanical model for quasi-brittle compressive failure of glass-microballoons/thermoset-matrix syntactic foams, Journal of the European Ceramic Society 34(11) (2014) 2605-2616.
N. Gupta, E. Woldesenbet, Hygrothermal studies on syntactic foams and compressive strength determination, Composite Structures 61(4) (2003) 311-320.
R.L. Poveda, G. Dorogokupets, N. Gupta, Carbon nanofiber reinforced syntactic foams: Degradation mechanism for long term moisture exposure and residual compressive properties, Polymer Degradation and Stability 98(10) (2013) 2041-2053.
C.S. Karthikeyan, S. Sankaran, Effect of Absorption in Aqueous and Hygrothermal Media on the Compressive Properties of Glass Fiber Reinforced Syntactic Foam, Journal of Reinforced Plastics and Composites 20(11) (2001) 982-993.
V. Sauvant-Moynot, N. Gimenez, H. Sautereau, Hydrolytic ageing of syntactic foams for thermal insulation in deep water: degradation mechanisms and water uptake model, J Mater Sci 41(13) (2006) 4047-4054.
V. Sauvant-Moynot, S. Duval, N. Gimenez, J. Kittel, Hot wet aging of glass syntactic foam coatings monitored by impedance spectroscopy, Progress in Organic Coatings 59(3) (2007) 179-185.
F. Grosjean, N. Bouchonneau, D. Choqueuse, V. Sauvant-Moynot, Comprehensive analyses of syntactic foam behaviour in deepwater environment, J Mater Sci 44(6) (2009) 1462-1468.
V. Sauvant-Moynot, Gimenez, N., Adrien, J., Maire, E., X-Ray Microtomography for a Better Understanding of Syntactic Foam Performance and Limits in Ultra Deep Water, Oilfield Engineering with Polymers 2006, London, England, 2006, p. 7.
N. Gimenez, V.r. Sauvant-Moynot, H. Sautereau, Wet Ageing of Syntactic Foams Under High Pressure/High Temperature in Deionized Water, (41979) (2005) 205-210.
J. Lachambre, E. Maire, J. Adrien, D. Choqueuse, In situ observation of syntactic foams under hydrostatic pressure using X-ray tomography, Acta Materialia 61(11) (2013) 4035-4043.
J.J.A. DeRuntz, O. Hoffman, The Static Strength of Syntactic Foams, Journal of Applied Mechanics 36(3) (1969) 551-557.

(56) References Cited

OTHER PUBLICATIONS

P. Viot, Hydrostatic compression on polypropylene foam, International Journal of Impact Engineering 36(7) (2009) 975-989.
O. Wurl, J.P. Obbard, Distribution of organochlorine compounds in the sea-surface microlayer, water column and sediment of Singapore's coastal environment, Chemosphere 62(7) (2006) 1105-1115.
V. Tornero, G. Hanke, Chemical contaminants entering the marine environment from sea-based sources: A review with a focus on European seas, Marine Pollution Bulletin 112(1) (2016) 17-38.
V. Shunmugasamy, D. Pinisetty, N. Gupta, Viscoelastic properties of hollow glass particle filled vinyl ester matrix syntactic foams: effect of temperature and loading frequency, J Mater Sci 48(4) (2013) 1685-1701.
G. Tagliavia, M. Porfiri, N. Gupta, Vinyl Ester-Glass Hollow Particle Composites: Dynamic Mechanical Properties at High Inclusion Volume Fraction, Journal of Composite Materials 43(5) (2009) 561-582.
D. Romanzini, A. Lavoratti, H.L. Ornaghi Jr, S.C. Amico, A.J. Zattera, Influence of fiber content on the mechanical and dynamic mechanical properties of glass/ramie polymer composites, Materials & Design 47(0) (2013) 9-15.
A. Kadkhoda Ghamsari, E. Zegeye, E. Woldesenbet, Viscoelastic properties of syntactic foam reinforced with short sisal fibers, Journal of Composite Materials (2013).
B. John, R. Nair, Update on Syntactic Foams, 2010.
S.C. George, S. Thomas, Transport phenomena through polymeric systems, Progress in Polymer Science 26(6) (2001) 985-1017.
R. Rubio, A. Sahuquillo, G. Rauret, P. Quevauviller, Determination of Chromium in Environmental and Biological Samples by Atomic Absorption Spectroscopy: A Review, International Journal of Environmental Analytical Chemistry 47(2) (1992) 99-128.
R.J. Vitale, G.R. Mussoline, K.A. Rinehimer, Environmental Monitoring of Chromium in Air, Soil, and Water, Regulatory Toxicology and Pharmacology 26(1) (1997) S80-S85.
B. John, Reghunadhan, Nair, C.P., Syntactic Foams, in: S.H. Goodman, Dodiuk-Kenig, H. (Ed.), Handbook of Thermoset Plastics, Elsevier, Chapter 13, 2014.
N. Gupta, D. Pinisetty, V.C. Shunmugasamy, Introduction, in: N. Gupta, D. Pinisetty, V.C. Shunmugasamy (Eds.), Reinforced Polymer Matrix Syntactic Foams: Effect of Nano and Micro-Scale Reinforcement, Springer International Publishing, Cham, , Chapter 1, 2013, pp. 1-8.

* cited by examiner

SYNTACTIC FOAMS AS MECHANICALLY-TRIGGERED CAPTURE VEHICLES

CROSS-REFERENCE TO RELATED APPLICATION

The present application claims the benefit of U.S. Provisional Patent Application No. 62/981,116, filed Feb. 25, 2020, the disclosure of which is hereby incorporated herein by reference in its entirety.

BACKGROUND

Syntactic foams are lightweight composite materials with utility in applications that require exposure to challenging conditions. [1] For example, the high buoyancy, high compressive strength, and low moisture uptake renders many syntactic foams suitable for use in marine applications, including components of spring buoys in deep-water moorings, [2] underwater unmanned vehicles, [3] and thermal insulators for deepwater pipelines during oil and gas production. [4, 5] In the aerospace sector, syntactic foams have been used for components that require lightweight and robust materials, such as spacecraft launch and re-entry vehicles, [6-8] and a multitude of components for aircraft. [9] Many consumer products also benefit from the combined lightness and strength of syntactic foams, such as sporting goods [10] and automotive components. [11]

The functional diversity of syntactic foams stem from their unique material composition. Syntactic foams include hollow microparticles distributed throughout a cured polymer matrix, existing in an overall closed cell microstructure arrangement without interconnected porosity. [12] This structural composition generates lightweight and low density material while simultaneously enabling tunable moduli and adequate mechanical strength for diverse applications. Moreover, these materials are capable of enduring high hydrostatic pressures with minimal absorption of water to maintain structural integrity in demanding aqueous environments. [13] Syntactic foams are typically formulated to align with the intended applications by selecting combinations of hollow microparticles and polymer matrix to ensure targeted performance. Various combinations of microparticles and polymer matrices have been reported, including hollow microparticles that comprise carbon, [14, 15] glass, [16, 17] and ceramic, [18, 19] and polymer matrices comprising epoxy, [20, 21] phenolic, [22] polyurethane, [23] bismaleimides, [24] and cyanate esters resins. [25] Processing parameters also require considerations, as the mixing procedures prior to the resin cure can result in air voids entrapped with in the material that result in added porosity to the final product.

To ensure long-term performance under demanding conditions, various physical properties of syntactic foams have been characterized under simulated conditions including mechanical properties and moisture uptake. [13] Failure modes for syntactic foams modes have been studied under compressive forces [26] and hydrostatic loading. [27] Uniaxial compression of epoxy-based syntactic foams with hollow glass spheres have resulted in with various macroscopic failure modalities. [16, 28-30]

The use of syntactic foams in marine environments has prompted many reports that describe water uptake into these materials after exposure to various testing conditions. Studies of hygrothermal aging of syntactic foams without applied pressure have reported moderate moisture ingress over time, resulting in weight gains typically below 10%. [5, 31-33] For example, a study with a syntactic foam including an epoxy matrix (diglycidyl ether of bisphenol-A (DGEBA) and triethylene tetramine) and glass microspheres reported a 6.7% weight gain after nearly two months of immersion in deionized water at 70° C. [31] More substantial weight gains from moisture ingress into syntactic foams have also been reported. Notable studies with an epoxy resin syntactic foam (DGEBA with 4,4'-methylenebis (3-choloro-2,6-diethylaninilne (MCDEA) and glass spheres) reported mass gains of >50% after exposure to heated deionized water without applied pressure. [34-36] In one example, the DGEB/MCDEA syntactic foams with 55 vol % of glass microspheres syntactic foams showed nearly 60% weight gain after immersion in deionized water at 100° C. for 18 months. [35] The application of temperature in combination with hydrostatic pressure to syntactic foams have also been evaluated. [37, 38] For example, water ingress into epoxy-syntactic foams resulted in 53% weight gain after immersion in deionized water at 120° C. at 3 bar for 71 days. [37]

The ingress of liquid into syntactic foams requires consideration of various factors, including applied environmental conditions, chemical properties of the polymer matrix and hollow spheres, and void spaces within the material. Lafebvre et al. reported a water uptake model for syntactic foams under different aging parameters that involve three hydration mechanisms: hydration of the matrix, hydration of glass, and filling of the microbubbles cavities. [5] The processing parameters and quantity of microspheres loaded into the polymer matrix are important, as the spatial distribution of microsphere interfaces and void spaces may influence the routes of liquid ingress. Lachambre et al. reported fluid ingress into polypropylene syntactic foams under hydrostatic pressure and suggested the network of microsphere interfaces could potentially form a path for the surrounding fluid. [39] The use of coatings on syntactic foams can prevent liquid penetration into samples under pressure, such as shown with water-based clay coatings on samples within a pressurized hydraulic oil or silicone gel coatings on polypropylene foams in pressured water. [40, 41]

SUMMARY

The utility of syntactic foams by leveraging inherent characteristics of these materials can be expanded. The distinctive architecture of syntactic foams, involving the vacant cavities encased within collapsible shells, can serve as receptacles for receiving and holding environmental constituents. The vacant spaces within hollow glass microspheres can be used as sampling reservoirs for the uptake of components within an environment, following a specific environmental trigger. This notion can be valuable for certain applications, such as exploration and production for oil and gas or monitoring the quality of marine water, both which require assessing the constituents in high-pressure environments. [42, 43] To our knowledge, the concept of using syntactic foams as capture reservoirs has not been considered. As discussed herein, we broaden the value of syntactic foams, or similarly related void-space materials, by describing controlled liquid uptake by epoxy-based syntactic foam formulations with an architecture of collapsed glass microspheres embedded within a polymer matrix.

Herein, the viscoelastic properties of epoxy-based syntactic foams, including hollow glass spheres embedded in an epoxy matrix, after exposure to conditions of high pressure and high temperature are described. The correlation of viscoelastic properties of different formulations of syntactic foams with the environmental conditions is shown. The utilization of environmental triggers, such as heat and pressure, to sequester environmental constituents within the hollow voids of the syntactic foams structure is explored, which may be applied to an environment-dependent sampling approach.

Accordingly, in an aspect of the invention, provided is an environmental constituent collecting vehicle including a syntactic foam, the syntactic foam including: a polymer matrix; and hollow microparticles.

In another aspect of the invention, provided is a method of collecting an environmental constituent including: providing an environmental constituent collecting vehicle including a syntactic foam including a polymer matrix and hollow microparticles to an environment; and collecting an environmental constituent from the environment with the environmental constituent collecting vehicle, wherein collection of the environmental constituent is triggered by pressure and/or temperature in the environment.

In yet another aspect of the invention, provided is a method of analyzing an environment comprising: providing an environmental constituent collecting vehicle comprising a syntactic foam to an environment, the syntactic foam comprising a polymer matrix and hollow microparticles; and collecting an environmental constituent from environment with the environmental constituent collecting vehicle, wherein collection of the environmental constituent is triggered by pressure and/or temperature in the environment.

In yet another aspect of the invention, provided is a composite material comprising a polymer matrix and hollow microparticles, wherein: the polymer matrix comprises an epoxy resin formulation; and the hollow microparticles comprise glass microspheres.

In yet another aspect of the invention, provided is a method of collecting a sample from a deep-sea marine environment comprising: providing a vehicle for collecting the sample comprising a syntactic foam to the deep-sea marine environment, the syntactic foam comprising a polymer matrix and hollow microparticles; and collecting the sample from the deep-sea marine environment with the vehicle, wherein collecting of the sample is triggered by pressure and/or temperature in the deep-sea marine environment.

In yet another aspect of the invention, provided is a method of collecting a sample from an oil or gas well or pipeline comprising: providing a vehicle for collecting the sample comprising a syntactic foam to the oil or gas well or pipeline, the syntactic foam comprising a polymer matrix and hollow microparticles; and collecting the sample from the oil or gas well or pipeline with the vehicle, wherein collecting of the sample is triggered by pressure and/or temperature in the oil or gas well or pipeline.

In yet another aspect of the invention, provided is a method of monitoring quality of marine water comprising: providing a vehicle for collecting the sample comprising a syntactic foam to a marine water environment, the syntactic foam comprising a polymer matrix and hollow microparticles; collecting the sample from the marine water environment with the vehicle: and analyzing the sample for impurities or pollutants, wherein collecting of the sample is triggered by pressure and/or temperature in the marine water environment.

In yet another aspect of the invention, provided is a method of exploring for oil or gas comprising: providing a vehicle for collecting the sample comprising a syntactic foam to a potential oil or gas field, the syntactic foam comprising a polymer matrix and hollow microparticles; collecting the sample from the potential oil or gas field with the vehicle; and analyzing the sample for oil or gas presence, wherein collecting of the sample is triggered by pressure and/or temperature in the potential oil or gas field.

In yet another aspect of the invention, provided is a method for determining the amount of a metal or a metal salt in an environment comprising: providing a vehicle for collecting an environmental constituent comprising a syntactic foam to the environment, the syntactic foam comprising a polymer matrix and hollow microparticles; collecting the environmental constituent from the environment with the vehicle; and analyzing the environmental constituent for the metal or the metal salt, wherein collecting of the environmental constituent is triggered by pressure and/or temperature in the environment.

In yet another aspect of the invention, provided is a method of determining if metal contamination is present in an environment comprising: providing a vehicle for collecting an environmental constituent comprising a syntactic foam, the syntactic foam comprising a polymer matrix and hollow microparticles, to the environment; collecting the environmental constituent from the environment with the vehicle; and analyzing the environmental constituent for metal contamination, wherein collecting of the environmental constituent is triggered by pressure and/or temperature in the environment.

BRIEF DESCRIPTION OF THE DRAWINGS

(FIG. 3A) Storage modulus and (FIG. 3B) tan delta curves for samples without environmental exposures. Samples include (i) ES-10K, (ii) ES-3K, (iii) ES-300, and (iv) ES-0.

(FIG. 9A) % Weight change and (FIG. 9B) Cr(III) within ES-300 samples after exposure to different conditions. ES-300 samples were immersed in solutions of either 100 mM Cr(III) acetate or 10 mM Cr(III) acetate for two hours.

DETAILED DESCRIPTION

Figure 1:
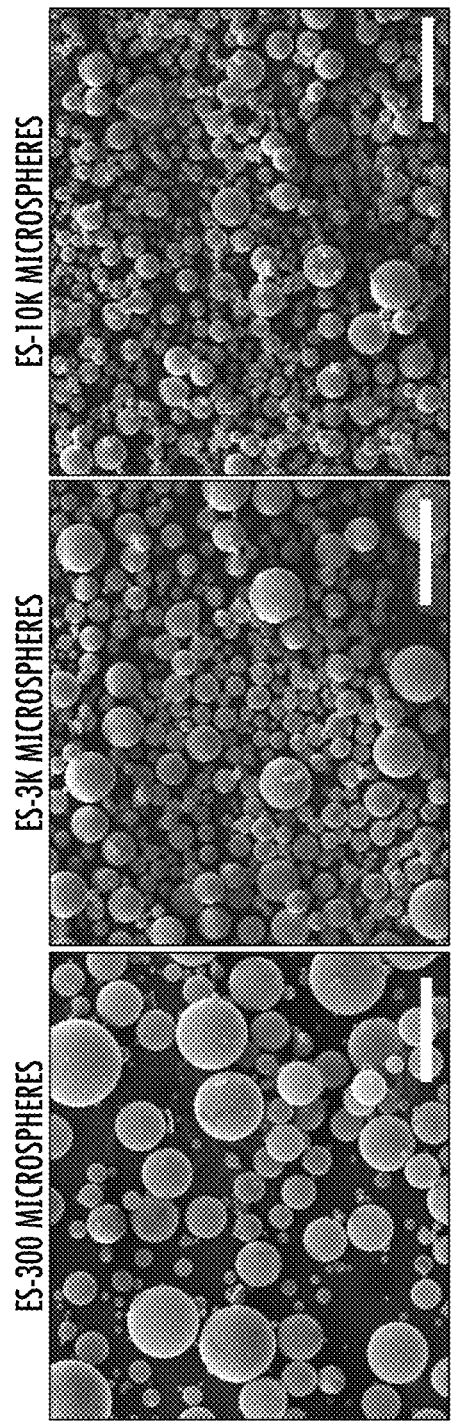
FIG. 1. SEM images of hollow glass spheres, as received from the manufacturer. The scale bars represent 100 μm.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical and scientific terms used herein have the same meaning as commonly understood by one of ordinary skill in the art to which this invention belongs.

Embodiments of the present inventive concept relate to a vehicle for collection of an environmental constituent, and methods of collecting environmental constituent for the purpose of, for example, analysis of the environment.

A "vehicle for collection," "collecting vehicle," "capture vehicle," and/or "capture reservoir" are intended to describe a device, medium, and/or system for collecting, for example, an environmental constituent, such as a sample of interest from an environment. The nature if the environment is not particularly limited, and may be, for example, a high pressure and/or high temperature environment, such as may be found in exploration and production for oil and/or natural gas, as may be found in monitoring the quality of marine water, or as may be found within a large scale chemical reactor, all of which may require assessment of environmental constituents or samples.

An "environmental constituent" is intended to describe a sample collected, obtained or retrieved from an environment of interest, wherein the sample may be subject to analysis in order to, for example, gain information regarding aspects of the environment of interest, or monitor the status of aspects of the environment of interest.

In some embodiments, the vehicle for collection of an environmental constituent may include a syntactical foam including, for example, hollow microparticles or microspheres distributed within a polymer matrix. The nature of the hollow microparticles/microspheres and/or polymer matrix is not particularly limited, and may be any suitable hollow microparticles/microspheres and/or polymer matrix may be used in the vehicle for collection according to embodiments of the present inventive concept that would be appreciated by one of skill in the art.

In some embodiments, the hollow microparticles/microspheres may be carbon, glass, and ceramic in nature. In some embodiments, the hollow microparticles/microspheres may be of glass. In some embodiments, the glass microparticles/microspheres may be of a particular isostatic or characteristic crush strength, for example, as determined by a pressure at which the glass microparticles/microspheres have a fractional survival of about 80%, 85%, or about 90%. In some embodiments, the glass microparticles/microspheres have a fractional survival that is about 90%. The crush strength rating of the glass microspheres may be any as appreciated by one of skill in the art, for example, about 250 psi, 300 psi, 400 psi, 500 psi, 750 psi, 2,000 psi, 3,000 psi, 4,000 psi, 5,500 psi 6,000 psi, 10,000 psi, 16,000 psi, 18,0000 psi, or about 28,000 psi. In an embodiment, the crush strength rating of the glass microspheres may be about 300 psi. In another embodiment, the crush strength rating of the glass microspheres may be about 3,000 psi. In still another embodiment, the crush strength rating of the glass microspheres may be about 10,000 psi.

In addition, the volume percent of the hollow microparticles/microspheres in the syntactical foam of the inventive concept is not particularly limited. For example, the volume percent of the hollow microparticles/microspheres may be about 30 volume % to about 60 volume %. In some embodiments, the volume percent of the hollow microparticles/microspheres may be, for example, about 50 volume %.

In some embodiments, the polymer matrix may be an epoxy, phenolic, polyurethane, bismaleimide, or cyanate ester resin. In some embodiments, the polymer matrix may be an epoxy-based matrix/resin, for example, an epoxy-based resin including diglycidyl ether of bisphenol A (EPON™ 828) (Hexion), butyl glycidyl ether (HELOXY™ 61) (Hexion), and triethylene tetraamine (TETA) (Hexion). The stoichiometric ratio of monomers may be a 1:2 ratio of diamine:diepoxide (TETA:EPON), but is not limited thereto, depending on the characteristic that may be desired. The polymer matrix of the syntactic foam, according to embodiments of the present inventive concept, may provide the syntactic foam with a particular glass transition temperature (Tg). The glass transition temperature of the polymer matrix/syntactic foam is not particularly limited. The Tg may be determined by, for example, dynamic mechanical analysis (DMA), wherein the Tg is taken from the maximum of the peak in the α-transition region of the tan delta curve. The Tg of epoxy resins typically may vary between about 50° C. and about 260° C. In some embodiments, the polymer matrix/syntactic foam may have a Tg of about 60° C. to about 110° C., about 70° C. to about 85° C., or about 75° C. to about 85° C. In some embodiments, the polymer matrix/syntactic foam has a Tg of about 80° C.

Furthermore, the structure, shape and/or size of the collecting vehicle is also not particularly limited, and the structure of the collecting vehicle may be of any form/shape that may be suitable for its intended use.

In other embodiments, the method for collecting an environmental constituent may include providing the collecting vehicle as described herein to an environment of interest. The environmental constituent may then be collected with the collecting vehicle. In some embodiments, collecting of the environmental constituent is initiated or triggered by an aspect or characteristic of the environment. For example, collecting of the environmental constituent may be initiated or triggered by pressure, and/or temperature of the environment.

The pressure and/or temperature at which collection of the environmental constituent may occur at a temperature and/or pressure in excess of standard temperature and/or pressure (STP, T=0° C., P=1 atm), or normal temperature and pressure (NTP, T=20° C., P=1 atm). Characteristics of the syntactic foam of the collection vehicle may be tailored so that collection of the environmental constituent may take place at a particular pressure and/or temperature.

For example, the pressure at which the environmental constituent is collected may be adjusted by choosing hollow microspheres having a particular isostatic crush strength, such as glass microspheres having a crush strength rating of, for example, about 300 psi, 3,000 psi, or about 10,000 psi, that are incorporated into the syntactic foam of the collecting vehicle. Similarly, the temperature at which the environmental constituent is collected may be adjusted by having a polymer matrix, for example, such as an epoxy resin formulation of the syntactic foam in the collecting vehicle, that results in the syntactic foam/epoxy resin formulation having a particular glass transition temperature (Tg) of, for example, about 60° C. to about 110° C., about 70° C. to about 85° C., or about 75° C. to about 85° C. In some embodiments, the Tg is about 80° C.

Accordingly, the pressure at which the environmental constituent is collected may occur at a pressure that exceeds the crush strength of the hollow microparticles/microspheres in the syntactic foam, and the temperature at which the environmental constituent is collected may occur at a temperature that exceeds the Tg of the polymer matrix/syntactic foam.

The environment from which the environmental constituent is collected from is also not particularly limited. In some embodiments, the environment from which the environmental constituent is collected from may be an environment exposed to or subjected to high temperature and/or high pressure. For example, the environment may be a deep-sea marine environment, or an environment in an oil or natural gas well, natural gas fields, and/or in an oil or natural gas pipeline, including deep-water oil or natural gas wells, and/or in deep-water oil or natural gas pipelines, or the environment within a chemical reactor, for example, such as in large scale chemical reactors.

Analysis of the environmental constituent is not particularly limited, and may include, for example, analyzing or monitoring marine water for impurities or pollutants, exploring for or detecting oil or gas, detecting the presence of metals or metal salts, determining if metal contamination is present, and/or analyzing or monitoring, for example, reactions taking place in or reaction progress within a chemical reactor, such as within large scale chemical reactors.

Exemplary aspects of the present inventive concept will be further described in the following examples.

EXAMPLES

Materials and Methods

Syntactic Foam Preparation

All samples used were prepared using an epoxy resin formulation including diglycidyl ether of bisphenol F (EPON™ 828) (Hexion), butyl glycidyl ether (HELOXY™ 61) (Hexion), and triethylene tetraamine (TETA) (Hexion) as shown in the chemical structures below. Samples were prepared by combining the EPON™ 828 epoxy monomer (epoxide equivalent weight of 189)) with appropriate quantity of HELOXY™ 61 and mixing in a FlackTek Speed Mixer at 1500 rpm until thoroughly blended (typically 120 sec). Next, the hollow soda-lime-borosilicate microspheres (3M™ Glass Bubbles, S Series, SEM images shown in FIG. 1) were incorporated via spatula and subsequently mixed in the FlackTek at 1500 rpm. Lastly, TETA was added and mixed in the Flacktek Speed Mixer at 1500 rpm. After combining all components, the mixture was degassed by vacuum. All samples contained a stoichiometric ratio of monomers (i.e., 1:2 molar ratio of TETA:EPON™ 828) and 50 volume % of the hollow glass spheres. All material was used as received without further purification.

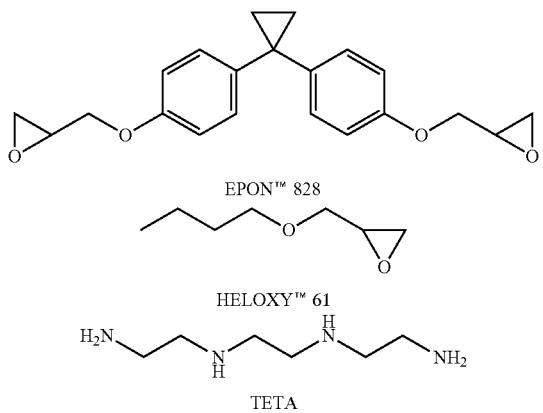

Chemical structures of monomers used.

DMA bars were prepared by pouring the pre-mixed monomers into aluminum molds with dimensions of 35 mm×12.7 mm×2.6 mm. All samples were first pre-cured at room temperature for at least six hours and subsequently cured at 80° C. for 60 minutes followed by 120° C. for another 120 minutes.

Characterization of Syntactic Foams

Dynamic Mechanical Analysis (DMA). Experiments were performed using a DMA instrument equipped with a single cantilever clamp (Q 800 TA Instruments). DMA tests were performed with a single frequency of 1 Hz and amplitude of 5 μm. The temperature ramp occurred from 30° C. to 140° C. at 2° C./minute. All DMA experiments were repeated at least three times for each condition. DMA samples immersed in liquid were dried until minimal change in weight was observed prior to analysis by DMA. The glass transition temperature was taken from the maximum of the peak in the a-transition region of the tan delta curve. At least three samples were tested per condition for all DMA experiments.

Density Measurement of Samples. The density of samples was measured using Archimedes' principle with a weight per gallon cup (Gardco). Briefly, a sample with known weight was placed in the cup of known volume and then filled with water to maximum capacity, enabling the determination of volume displaced by the sample.

Inductively Coupled Plasma Atomic Emission Spectroscopy (ICP-AES). To solubilize samples that contained Cr(III) for analysis via ICP-AES, samples were sealed within high pressure vessels (SEM Corporation) containing 5 mL of nitric acid and placed into the CEM Mars 5 Microwave system. The samples were heated at a slow ramp for 40 minutes until reaching 175° C. and held for 30 minutes. Upon completion of the heating, vessels were cooled to room temperature. The samples were then transferred to 50 mL volumetric vials and diluted 18 M Ohm water. ICP-AES analysis was performed using a Thermo iCAP 6500 ICP-OES. A set of calibration standards were prepared using NIST traceable stock standards, in the same acid matrix of the sample preparation (10% nitric acid in water). The instrument was then calibrated using these standards and then confirmed using a standard prepared from a separate line of dilution from the stock standard.

High Pressure High Temperature (HPHT) Studies

HPHT experiments were performed using a Fan Model 275 consistometer. DMA bars were immersed into a sealed bag containing approximately 15 mL of brine solution (8 wt % $CaCl_2$, 2wt % NaCl), loaded into the HPHT chamber, and maintained at the desired compressive pressure at 100° C. for two hours or near 35° C. for two hours without agitation. A reflux setup was used for DMA bar samples exposed to high temperature (i.e., 100° C.) for two hours at atmospheric pressure. For studies involving Cr(III) uptake, samples measured approximately 5 mm×1.25 mm×10 mm were placed into a solution of Chromium (III) acetate hydroxide (Sigma-Aldrich) and placed into the consistometer under specified conditions. After removal from the consistometer, all samples were rinsed with deionized water and the surfaces of the samples were dried prior to weighing by gently wiping the surface. The weight of the specimens were acquired before (W) and after immersion into solutions ($W_0$). The percentage of weight change (% $W_A$) was calculated using the formula:

$$\% W_A = [(W-W_0)/W_0] \times 100$$

Results and Discussion

Figure 2:
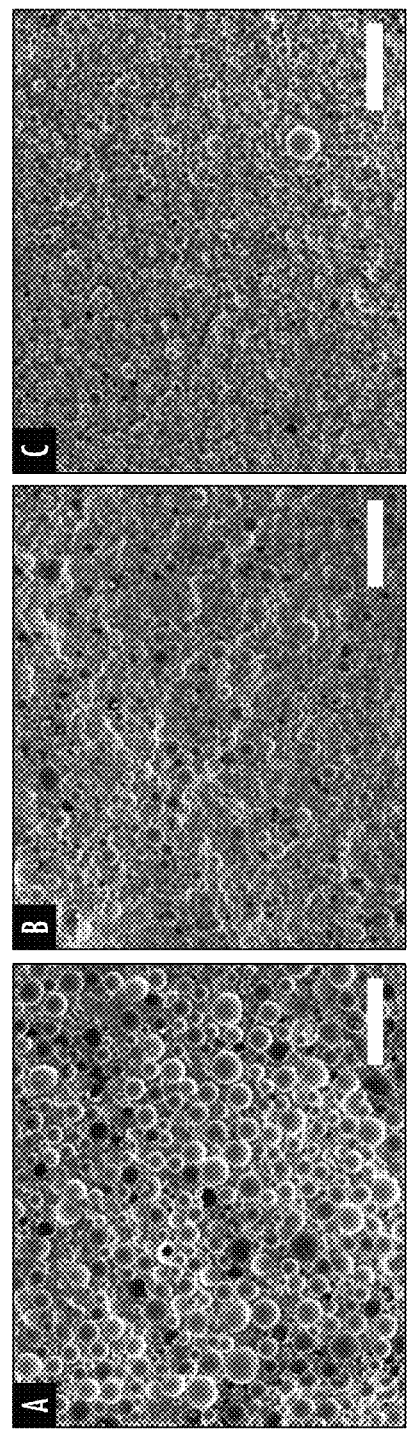
FIG. 2. SEM images showing the cross-sections of (A) ES-300, (B) ES-3K, and (C) ES-10K without environmental exposures. The scale bars represent 250 μM.

Properties of Epoxy Syntactic Foams Without Exposure to Pressure and Temperature To date, very few reports exist that have used DMA to examine the mechanical properties of syntactic foams after exposure simultaneously to high pressure and high temperature conditions. [5] Understanding the impact of environmental exposures on these materials not only advances the technology of syntactic foams, but also holds significant relevance to applications requiring performance in harsh environments, such as marine, aerospace, and energy applications. Here, we evaluated syntactic foams including an epoxy resin formulation filled with 50 volume percent of hollow glass spheres of different isostatic crush strengths (Table 1). The sample names represent the characteristic crush strength (target fractional survival of 90%) of hollow microspheres embedded within the epoxy resin: ES-300 (300 psi hollow microspheres), ES-3K (3000 psi hollow microspheres), and ES-10K (10,000 psi hollow microspheres). To evaluate the effects of the hollow glass microspheres on the material properties, the syntactic foam samples were compared to epoxy resin devoid of the hollow microspheres (i.e., ES-0). The densities of these samples differ (Table 1), showing that microspheres with lower crush strengths generate syntactic foams with lower densities. The morphology of these syntactic is shown in exemplary SEM images (FIG. 2), with hollow glass spheres are arranged throughout the epoxy polymer.

Figure 3A:
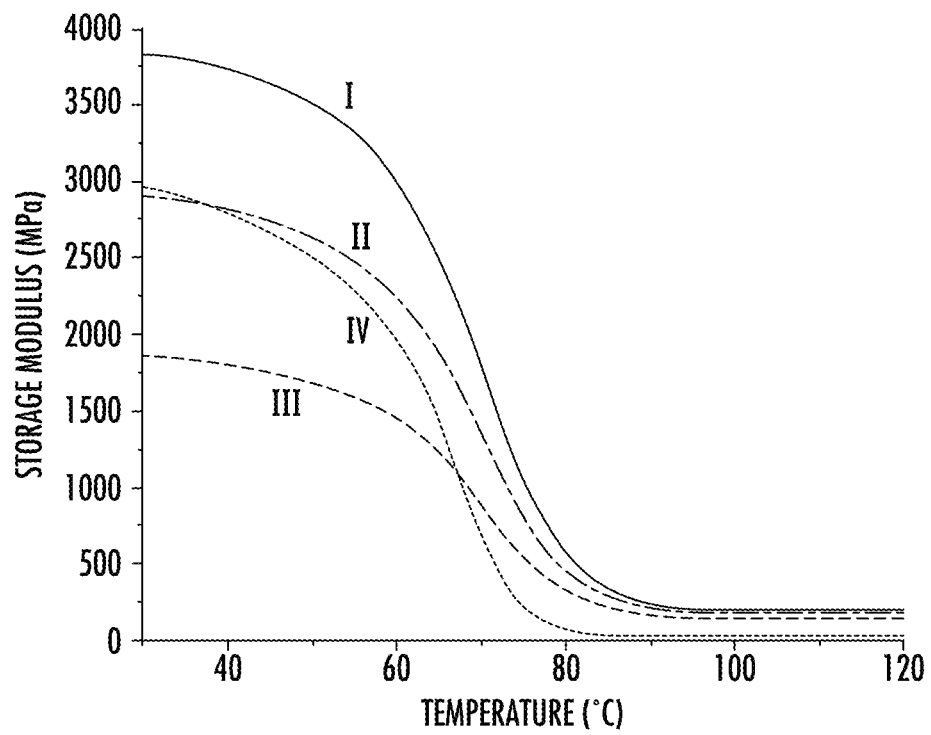
FIGS. 3A and 3B.
Figure 3B:
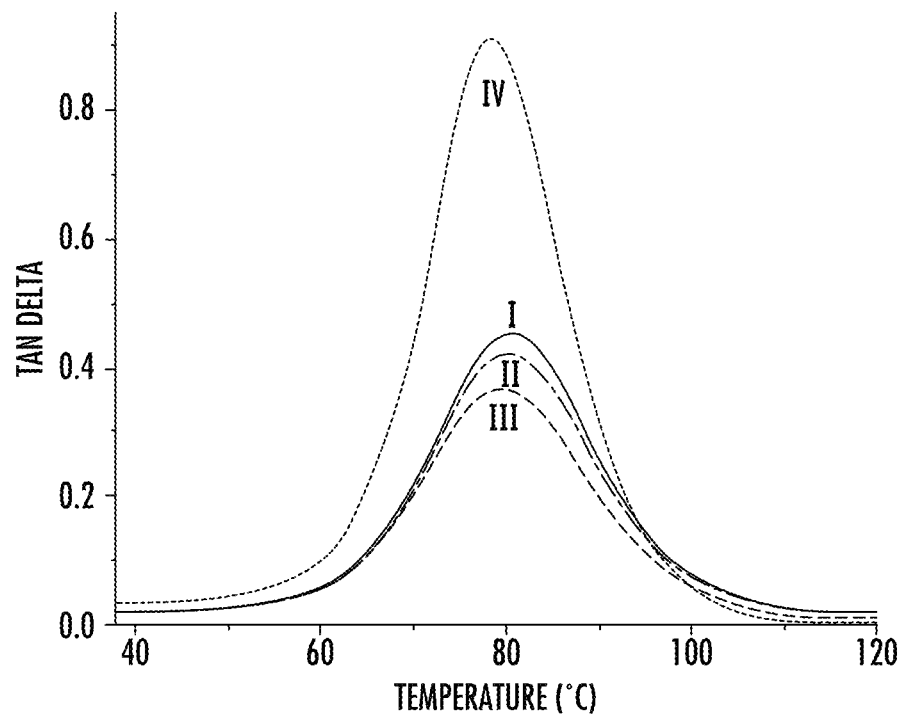

To first understand the viscoelastic properties of these formulations, DMA experiments were performed using samples without exposure to environmental factors (e.g., elevated temperature, pressure or moisture). The resultant storage modulus (E') and tan δ profiles in FIGS. 3A and 3B show that mechanical properties are affected by the presence and the type of hollow glass sphere within the matrix. For the storage modulus curves (FIG. 3A), a notable trend is evident within the rubbery plateau region, where filled systems exhibit higher E' values as compared to the neat epoxy material. For instance, the E' values (at 120° C.) are 21±1 MPa and 189±2 MPa for ES-0 and ES-10K samples, respectively (Table 2). The higher E' value within the rubbery plateau indicates an enhanced recovery from deformation which is typical of many syntactic foams and filled systems. Additionally, at temperatures below the Tg, the E' values (at 35° C.) for the filled systems rank as ES-10K>ES-3K>ES-300 (Table 2), likely resulting from differences in wall thickness of the hollow spheres. This trend aligns with previous reports, which showed that the storage modulus of syntactic foams increase with an increase in the wall thickness of the embedded hollow glass spheres. [44, 45] Notably, here the E' of the ES-10K and ES-3K samples are higher than the neat epoxy resin, which could result from the reinforcement of these hollow spheres.

The tan δ profiles in FIG. 3B show a considerable difference between neat epoxy resin and the syntactic foam samples. As previously reported for filled systems, [46, 47] the syntactic foams here exhibit a lower maximum tan δ values as compared to neat resin, which results from constrained movement of polymer chains in the presence of the hollow spheres. Also evident from FIG. 3B is that the inclusion of hollow glass spheres slightly increases the temperature at the tan δ peak, which is used to calculate the Tg in these studies. For example, the peak tan δ temperature increases from 78° C. (±1) to 80° C. (±0.4) for ES-0 and ES-300 samples, respectively (Table 2).

Properties of Epoxy Syntactic Foams after Exposure to HPHT Conditions

Figure 4A:
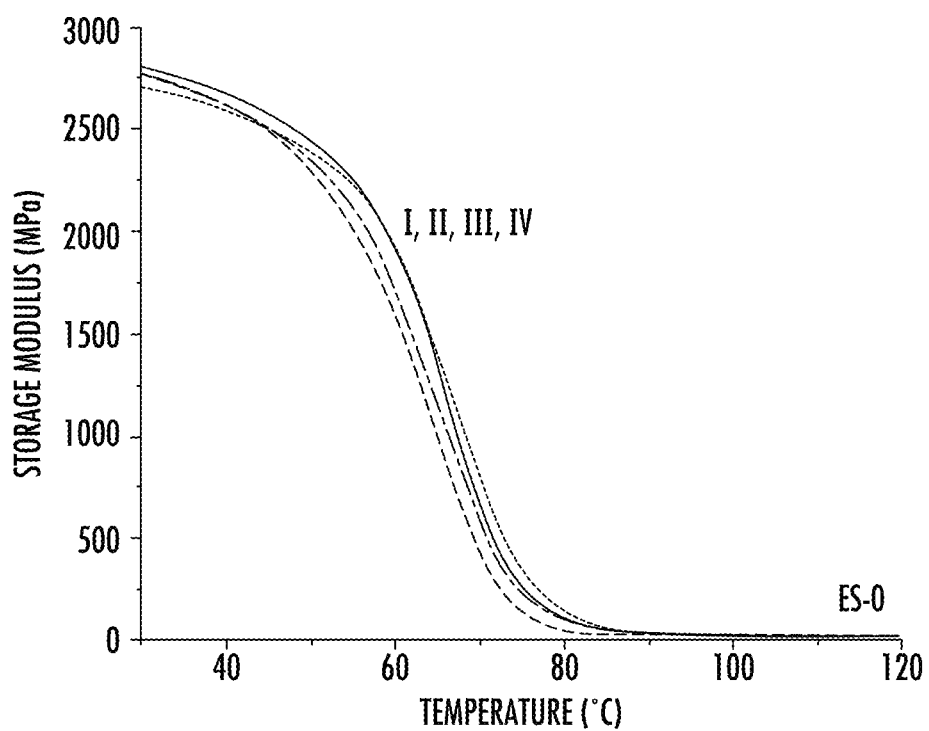
FIGS. 4A-4D. Representative storage modulus curves for (FIG. 4A) ES-0, (FIG. 4B) ES-300, (FIG. 4C) ES-3K, and (FIG. 4D) ES-10K after exposure to (ii) 1500 psi at 100° C., (iii) 7000 psi at 100° C., and (iv) 15,000 psi at 100° C. for two hours in saline solution (8 wt % $CaCl_2$, 2 wt% NaCl). Formulations without exposure to any environmental conditions (i) are included for comparison.
Figure 4B:
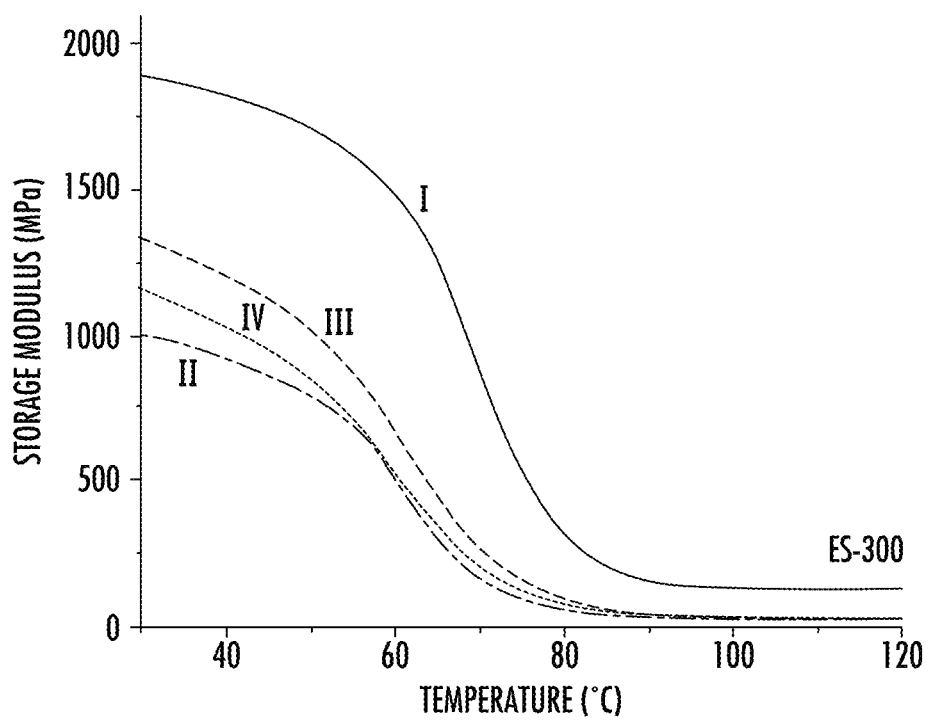
Figure 4C:
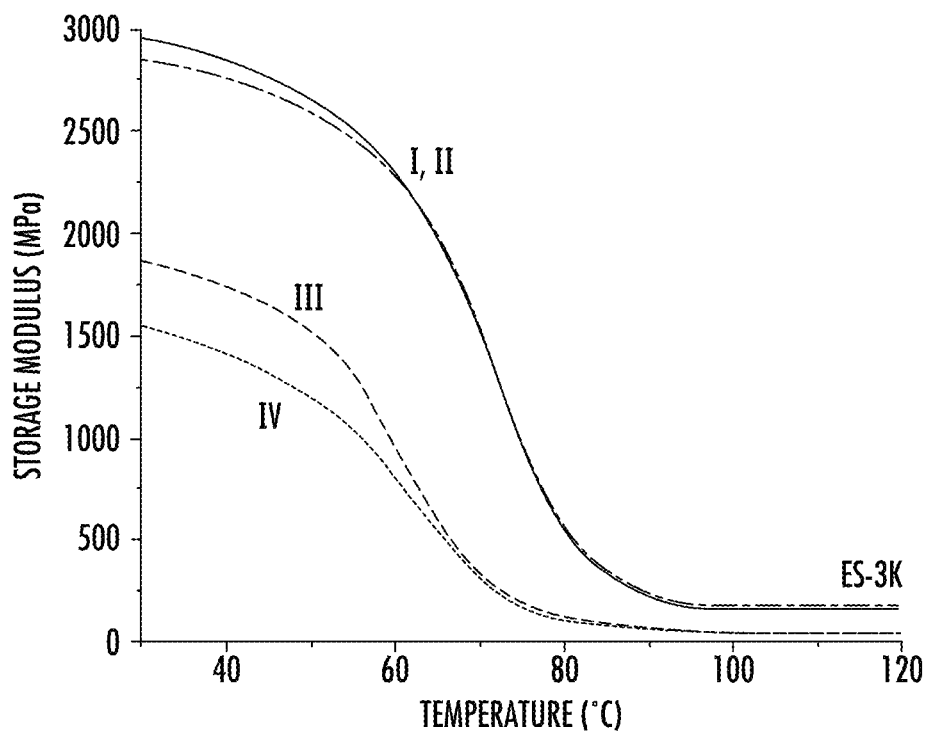
Figure 4D:
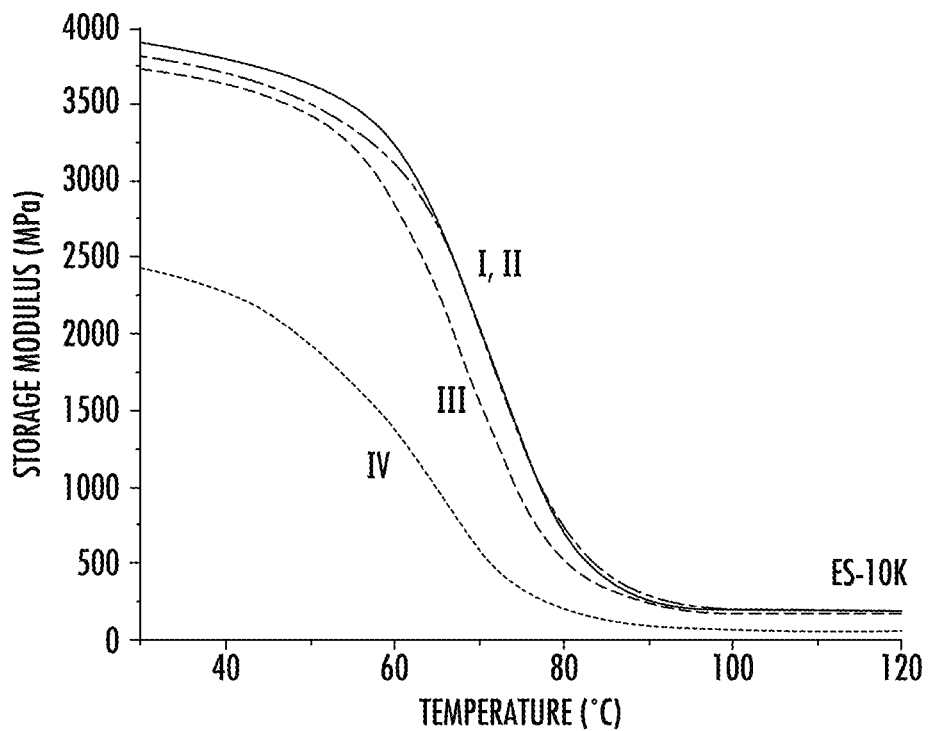

The mechanical properties of the syntactic foam samples were evaluated after exposure to 100° C. in saline solution (8 wt % $CaCl_2$, 2 wt % NaCl) at three different pressures: 1500, 7000, and 15,000 psi. We reasoned that the isostatic crush strength of the hollow glass spheres within the epoxy matrix, coupled with the exposure to pressure and temperature, would dictate the resultant microstructural features and associated viscoelastic properties of the material. The storage modulus profiles in FIGS. 4A-4D and compiled data in Table 3 support this concept, revealing that syntactic foams exposed to pressures above the isostatic crush strength of the embedded hollow glass spheres exhibit a drastic reduction in the storage modulus values. For example, at 35° C. the storage modulus for the ES-3K sample is 2865 (±52) MPa after exposure to 1500 psi but decreases to 1562 (±68) MPa after exposure to 15,000 psi, which is above the isostatic crush strength of the spheres of 3000 psi. Importantly, the samples were dried prior to performing the DMA experiments to substantially eliminate the effects of the water uptake during mechanical analysis (as discussed in the following section). Material devoid of hollow glass spheres exhibits near identical storage modulus profiles with and without exposure to different pressures at 100° C. (FIG. 4A). After removal from the HPHT consistometer, samples retained macroscopic integrity without cracks or deformations from visual observation.

Figure 5:
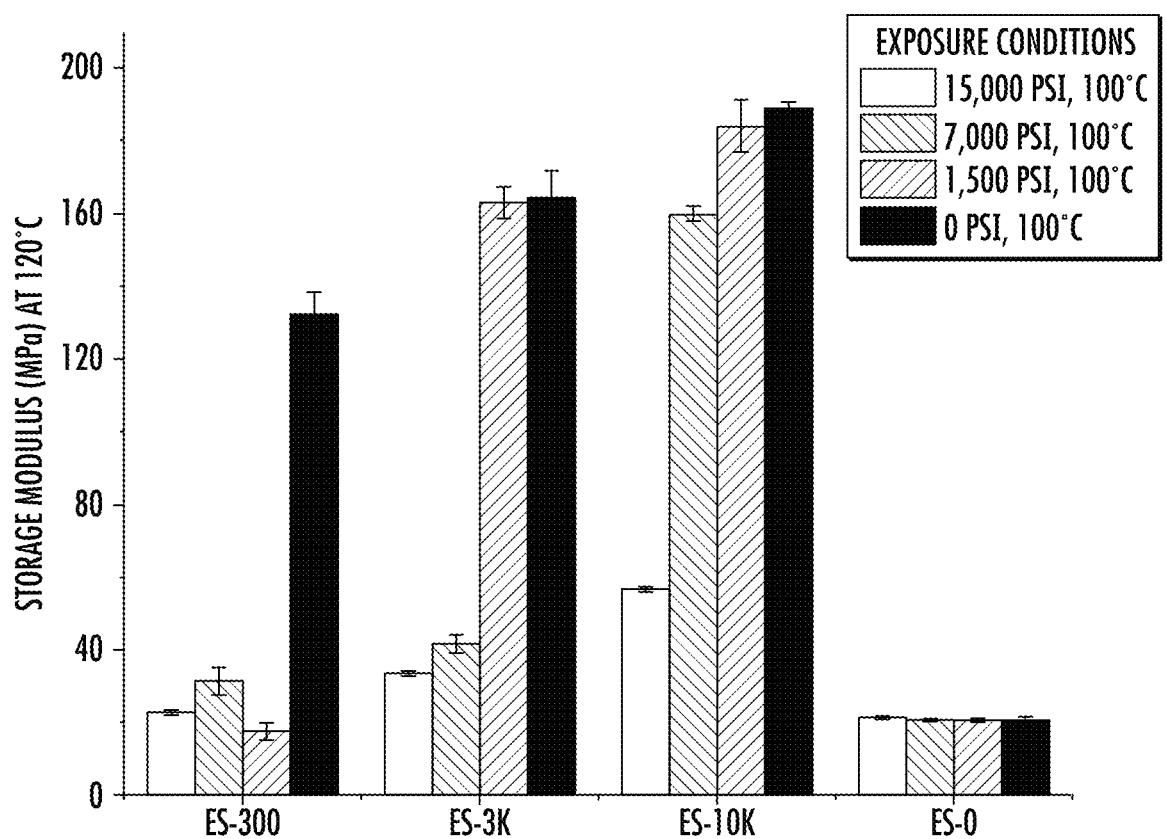
FIG. 5. The storage modulus at 120° C. in the rubbery plateau region for different syntactic foam samples after a two-hour exposure to different pressures in high saline solution (8 wt % $CaCl_2$, 2 wt% NaCl) at 100° C.

Interestingly, the E' values in the rubbery plateau region are greatly affected by the crush strengths of the spheres and the exposed pressures and temperatures. When the hollow glass spheres remain intact (i.e., exposure to pressures below the sphere isostatic crush strength), the E' values in the rubbery region remain higher than the E' values of the unfilled neat epoxy sample (ES-0). However, exposing samples to pressures above the sphere crush strength results in a significant drop in the E' values (FIG. 5). In one example, a greater than seven-fold decrease in the storage modulus at 120° C., from 132 (±6) MPa to 17 (±2) MPa, occurs with the ES-300 sample after exposure to 1500 psi at 100° C. for two hours. This trend suggests that reinforcements between the epoxy polymer and the spheres are greatly diminished after the collapse of the hollow spheres, enabling greater polymer chain movement in the rubbery plateau region. Conversely, hollow glass spheres that remain intact permit recovery from applied deformation and therefore exhibit higher storage modulus values. A similar observation was reported for syntactic foams reinforced with sisal fiber that showed higher storage modulus in the rubbery region, as compared to unfilled materials. [47] Lefebvre et al. reported a decrease in E' after aging of syntactic foams (i.e., epoxy, polypropylene, and polyurethane materials filled with glass microspheres) due to plasticization of the polymer matrix. [5] The epoxy-based matrix (ES-0 sample) as discussed herein did not show substantial differences in the E' values after exposure to various pressures and temperatures.

Figure 6A:
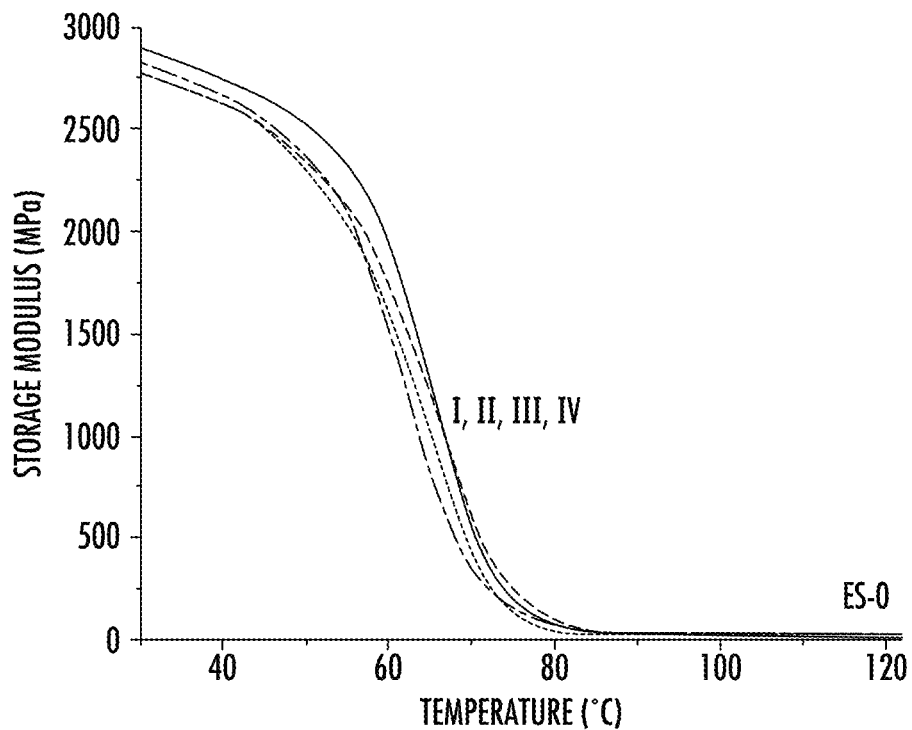
FIGS. 6A-6D. Representative storage modulus curves for (FIG. 6A) ES-0, (FIG. 6B) ES-300, (FIG. 6C) ES-3K, and (FIG. 6D) ES-10K. Storage modulus curves show formulations after exposure to (ii) 100° C. without additional pressure, (iii) 35° C. and 7000 psi, and (iv) 100° C. at 7000 psi. Samples for two hours in saline solution (8 wt % $CaCl_2$, 2 wt % NaCl). Formulations without exposure to any environmental conditions (i) are included for comparison.
Figure 6B:
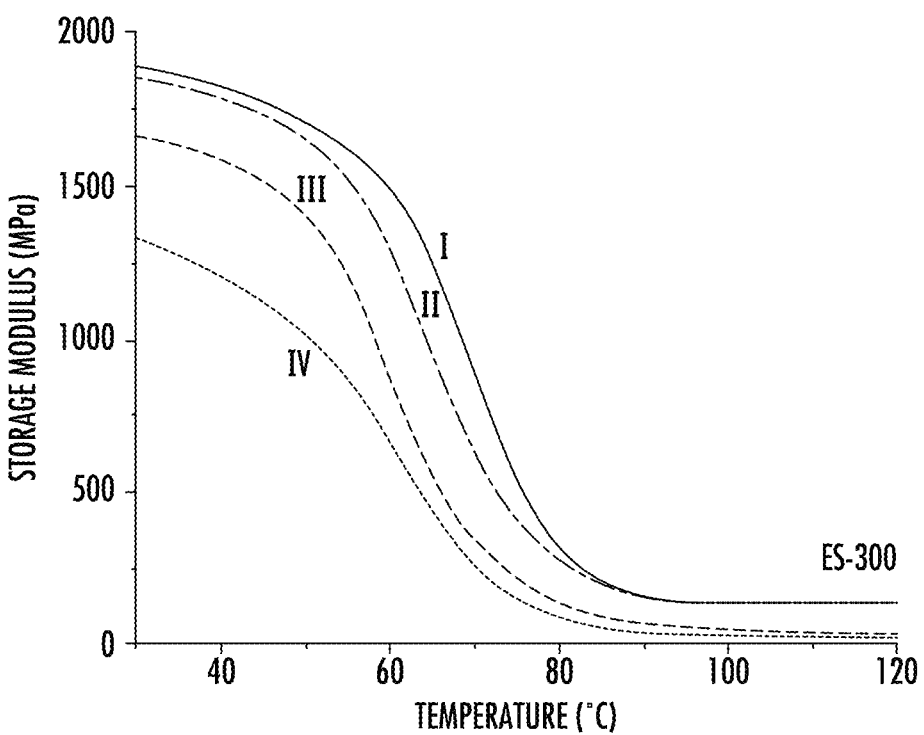

The samples exposed to high pressures thus far have also occurred at 100° C., which is above the glass transition temperature of the material of approximately 80° C. (Table 2). To further understand the specific effects of pressure and temperature separately, the mechanical properties of samples were compared after exposure to various conditions for two hours: 7000 psi at 100° C., 7000 psi at 35° C., and no applied pressure at 100° C. For all samples, the E' profiles remain nearly unaffected after exposure to 100° C. without applied pressure, which supports the requirement for elevated pressure to disrupt the mechanical properties of the syntactic foam. As expected, the E' profiles of samples devoid of hollow spheres (FIG. 6A) and samples containing spheres with the highest isostatic crush strength of 10,000 psi (ES-10K) (FIG. 6D) also remain relatively unaffected from all exposures, further reinforcing the necessity of damaged spheres to cause a reduction in storage modulus.

Figure 6C:
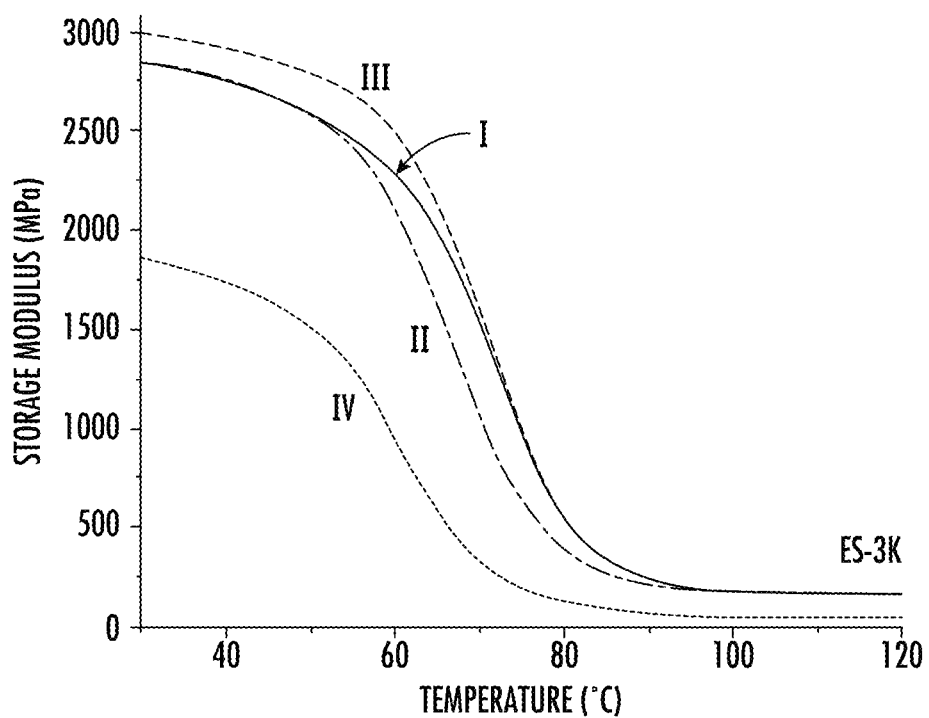
Figure 6D:
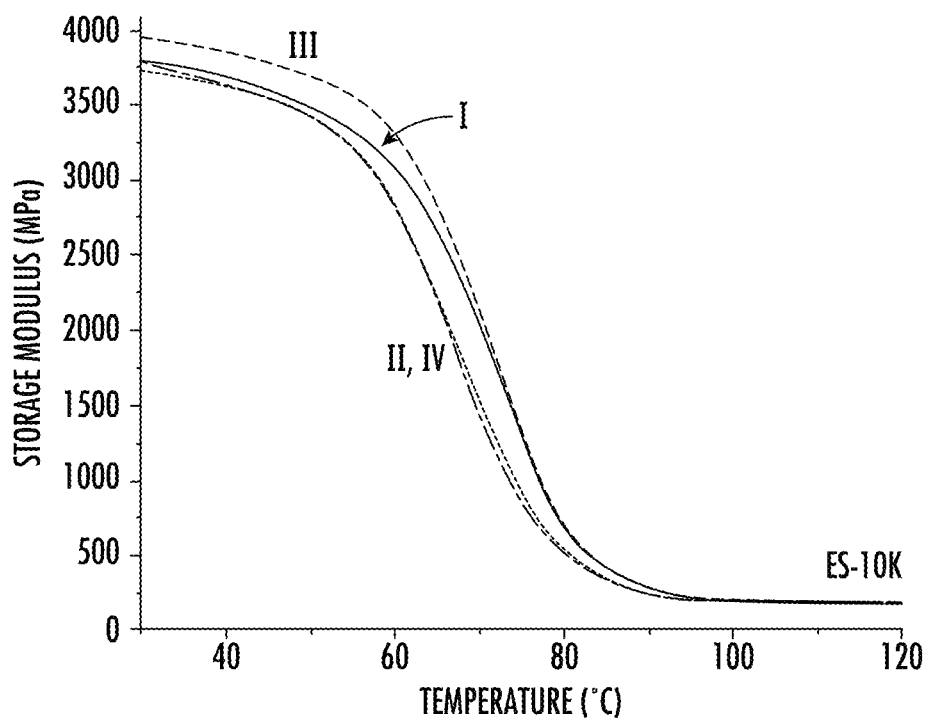

Samples containing spheres with isostatic crush strength of 300 psi (ES-300) (FIG. 6B) display a lowered E' after exposure to 7000 psi, even without application of temperature above the Tg. For instance, the storage modulus (at 35° C.) of the ES-300 samples dropped 75%, from 132±6 MPa to 33±3 MPa, after exposure to 7000 psi at 35° C., demonstrating that the hollow spheres within the ES-300 formulation rupture even below the Tg of the epoxy material. Conversely, FIG. 6C shows that the ES-3K samples require the combination of temperature and pressure to significantly reduce the storage modulus profiles under these conditions. For example, the E' (at 120° C.) is 174±5 MPa and 42±3 MPa after exposure to 7000 psi at 35° C. and 7000 psi at 100° C., respectively.

The differences in mechanical response between ES-300 and ES-3K samples may be explained by the level of pressure exposure. These studies suggest that a threshold pressure and temperature must be reached to enable the rupture of the hollow spheres and resultant reduction in mechanical properties. At an exposure of 7000 psi, the ES-300 samples experience a pressure that is 23-fold higher than the isostatic pressure tolerance of the sphere, whereas the ES-3K samples only experience a pressure that is 2.3-fold higher than the isostatic pressure tolerance of the spheres. In addition to pressure, the Tg of the matrix likely influences the microsphere rupture and would require characterization for each formulation.

Taken as a whole, the results in this section demonstrate that the exposure of syntactic foam samples to high pressure, high temperature conditions markedly affects the resultant viscoelastic properties in a manner that directly correlates with the composition of the hollow spheres and the applied conditions. In particular, samples embedded with hollow spheres including isostatic crush strengths less than the applied pressures exhibit a drastic reduction in E' profiles, likely resulting from degradation of microstructural features from crushed hollow spheres. The destruction of the closed-cell arrangement of the syntactic foam results in a material with similarities to open-cell foams, which typically show lower mechanical properties. [12] The ability to utilize this property to tune degradation properties through choice of sphere filler is further explored in the following section by focusing on the uptake and capture of environmental constituents.

Controlled Uptake of Environmental Constituents into Syntactic Foams

Figure 7:
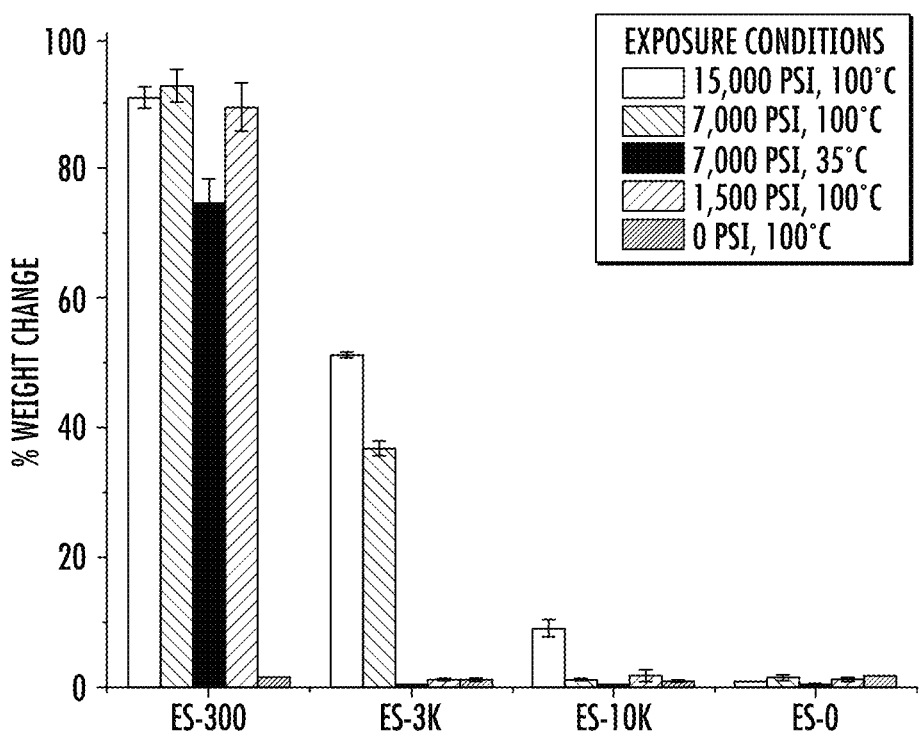
FIG. 7. Percent weight change of samples (n=3 each of ES-300, ES-3K, ES-10K, ES-0) after exposure to different conditions for two hours in brine solutions (8 wt % $CaCl_2$, 2 wt % NaCl).

The hollow microspheres within syntactic foams, including collapsible shells that enclose empty cavities, can serve as receptacles to capture and retain environmental constituents. Here, we explore controlled uptake of environmental constituents into the epoxy-based syntactic foams under high temperature and pressure. To first explore this concept, samples were subjected to different pressures and temperatures in brine solution for two hours and the samples were subsequently weighed (FIG. 7). The results show that applied pressure affects uptake of liquid into the samples. ES-300 samples, which contain microspheres with the lowest isostatic crush strength of 300 psi and the thinnest microsphere walls, exhibit the greatest weight gain after exposure to high pressures. For example, ES-300 samples gained 93% (±3%) after exposure to 7000psi at 100° C. for two hours, but only gained 1% (±0.1%) when exposed to atmospheric pressure at 100° C. for two hours. ES-3K samples also gained considerable weight when exposed to pressures above the crush strength of the microspheres at 100° C., showing a weight gain of 51% (±0.4%) and 37% (±1%) for exposure to 15,000 psi and 7,000 psi, respectively. When exposed to pressure below the crush strength of embedded microspheres (1,500 psi at 100° C.), ES-3K samples showed minimal a weight gain of 1% (±0.2%).

These results support the concept of liquid ingress resulting from the fracture of microspheres within the epoxy sample. As expected, epoxy samples devoid of hollow glass spheres (ES-0) show minimal weight change of less than 2% after exposure to all conditions. Syntactic foams are considered tertiary systems including a three-phase structure: matrix polymer, hollow voids within the microspheres, and open voids resultant of air entrapment during processing. [48] Weight gain during these exposures, therefore, likely occur due to liquid ingress into voids created by broken spheres and as well as air pockets resultant of sample processing and possibly diffusion through the polymer matrix.

Figure 8:
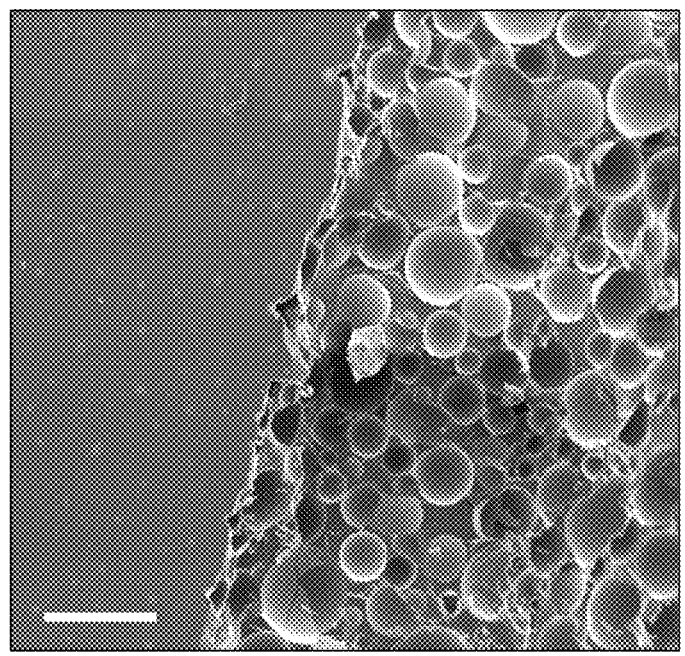
FIG. 8. SEM image showing the cross-section of a 1 mm thick film including ES-300. The left portion of the image shows the smooth surface of the sample that encases the hollow glass spheres on the right portion of the image. The scale bar represents 100 μm.

The graph in FIG. 7 also shows that temperature affects the extent of liquid ingress into samples. For example, minimal weight gain occurs in ES-3K samples after exposure to 7000 psi at 35° C. (0.3% ±0.1%), as compared to exposure at 7000 psi at 100° C. (37% ±1%). At 100° C., these samples are above the Tg of the material (Table 2), resulting in higher segmental mobility of the polymer chains and enhanced transport through the polymer. [49] All samples resulted in the formation of a thin skin-like layer of epoxy that encompassed the hollow glass spheres. For example, FIG. 8 shows the cross-section of the ES-300 sample with a distinct distribution of hollow glass spheres at the interface of a thin epoxy skin that resides on the outside of the sample. The formation of this epoxy skin at the air interface likely results from the differences in interfacial tension and preferential migration of the hollow glass spheres within the interior of the syntactic foam material during the cure. Because samples used for the weight-gain experiments also exhibited this smooth outer surface, weight gain of the samples likely involves transport of liquid through the polymer or defects in the polymer skin to access void spaces created by broken spheres.

Figure 9A:
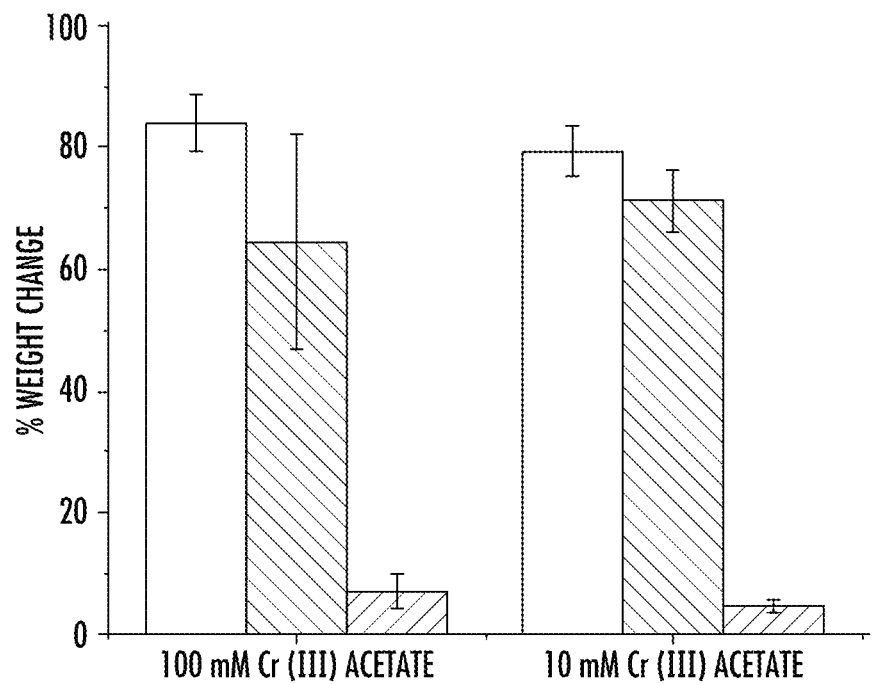
FIGS. 9A and 9B.
Figure 9B:
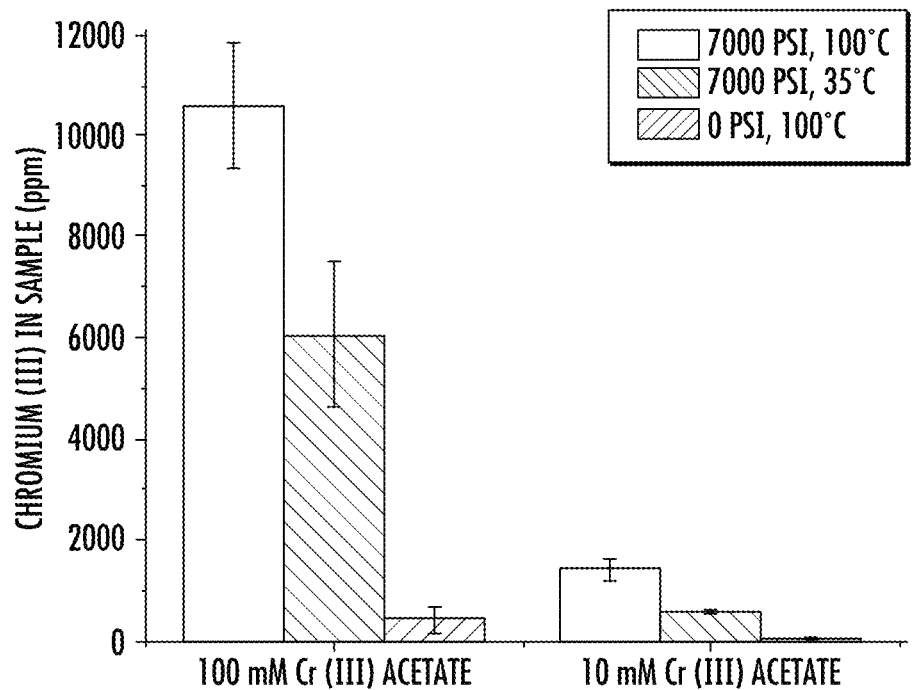

To further evaluate the capacity of syntactic foams to capture and store surrounding environmental constituents, samples were exposed to solutions of metal salts under different pressures and temperatures. Cr(III) was chosen as a model analyte in these studies, owing to the relevance of assessing environmental metals. [50, 51] To demonstrate capture of Cr(III) in the syntactic foam in a concentration-dependent manner, ES-300 samples were exposed to Cr(III) acetate solutions at 100 mM or 10 mM and under different applied pressures and temperatures for two hours. After the exposure, the samples were characterized for weight gain and uptake of Cr(III) via ICP-AES. As shown in FIG. 9A, ES-300 samples gained considerable weight after exposure to pressures above their crush strength (i.e., 7000 psi, 100° C. and 7000 psi, 35° C.) and minimal weight gain after exposure to 100° C. without applied pressure, in accordance to previous observations in FIG. 7. Importantly, FIG. 9B demonstrates that the quantity of Cr(III) captured within the syntactic foam depends on the concentration of the analyte in the surrounding solution. A change in concentration of the surrounding Cr(III) solution by an order of magnitude results in an accompanying order of magnitude change in the quantity of Cr(III) detected in the ES-300 samples. For instance, after exposure to 100 mM and 10 mM Cr(III), samples retained 10575 (±1228) ppm and 1430 (±209) ppm of Cr(III) respectively.

Figure 10:
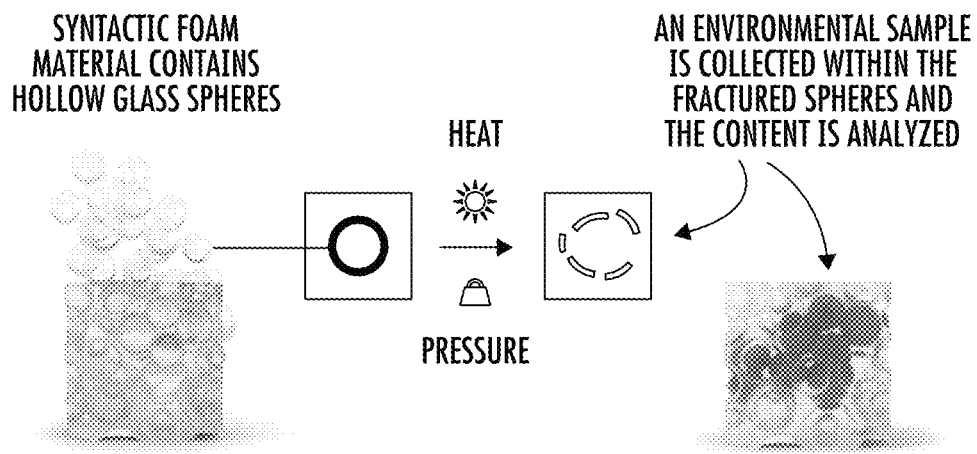
FIG. 10. A depiction of a syntactic foam of the present inventive concept serving as an on-demand receptacle capturing a sample in response to environmental conditions.

FIG. 10 depicts an exemplary embodiment of the inventive concept including a syntactic foam functioning as an on-demand receptacle to collect an environmental constituent as a result of an environmental trigger.

Figure 11:
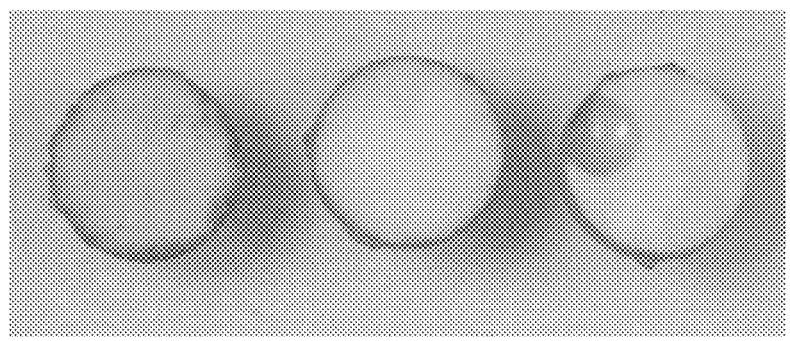
FIG. 11. Cross-sections of syntactic foam samples (ES-300, ES-3K, and ES-10K respectively, from left to right) after exposure to 7000 psi and 100° C. in a 500 µM solution of rhodamine-B.

To further demonstrate analyte capture by syntactic foams of the inventive concept, three syntactic foam samples (ES-300, ES-3K, and ES-10K) were exposed to a solution containing 500 µM of rhodamine-B. The samples were subjected to a pressure of 7000 psi and 100° C. After the samples were removed from the high pressure and high temperature conditions, the samples were sliced in half to reveal the interior, as shown in FIG. 11. The ES-300 sample (left) shows uptake of the rhodamine B solution, whereas the ES-10K sample (right) does not show uptake of the rhodamine B solution.

In summary, it has been demonstrated that this syntactic foam formulation can act as a capture vehicle to accurately and quantitatively capture proximate constituents in a manner dependent on the environmental conditions. Nearby constituents (e.g., Cr(III) and rhodamine-B) can transport into and reside within syntactic foams that are damaged microstructurally after exposure simultaneously to certain pressures (i.e., Pressure>isostatic crush strength of the hollow microspheres) and certain temperatures (i.e., Temperature>Tg of the polymer matrix). Of important note, all samples tested here retained macroscopic integrity, and were easily handled after environmental exposures. This property makes the syntactic foam a functional material suited for sampling environmental analytes, in a concentration sensitive manner, at predefined thresholds of pressure and temperature. For example, detecting the presence and quantity of an analyte within the environment that experiences certain conditions (e.g., pressures at certain ocean depths, geological formations) could be achieved with this approach by tuning polymer composition and sphere composition. Importantly, the dependency of liquid ingress into the samples would also require consideration of the spatial and temporal history of the sample. Samples were immersed within a single solution exposed to a defined temperature and pressure maximum. To employ this material as a sampling reservoir in real-world application, for example, samples may encounter multiple pressures and temperature combinations, which would require further analysis on transport behavior and capture of analytes into the material under fluctuating conditions.

An epoxy formulation (i.e., EPON™ 828, HELOXY™ 61, TETA) combined with different types of hollow glass spheres is described herein. Although not shown, it is expected that the epoxy matrix may influence the transport of components, disturbance of hollow spheres, and resultant mechanical properties after high pressure exposures. For example, the importance of matrix rigidity in the characteristics of sphere rupture in syntactic foams, with rigid matrices causing sudden, shear-dependent rupture and softer matrices causing a slower, progressive rupture under compressive tests have been described. [36, 37] The viscoelastic properties and liquid uptake may differ depending of choice of polymer.

Epoxy-based syntactic foams benefit many applications that require lightweight and strong materials. The functionality of syntactic foams ensues from the material composition, which includes hollow spheres distributed throughout a cured polymeric matrix. This composition with hollow spheres, however, can also result in structural limitations and loss of mechanical integrity after exposure to certain environmental conditions. We describe a new syntactic foam including a polymer formulation of EPON™ 828, HELOXY™ 61, and TETA, in combination with hollow glass microspheres with isostatic crush strengths of 300, 3000, and 10,000 psi. Mechanical properties of these materials before and after exposure to applied conditions, including various pressures (1500, 7000, 15,000 psi) and high temperatures (100° C.) are detailed. Samples including hollow glass spheres with isostatic crush strengths less than the applied pressures exhibit a drastic reduction in E' profiles, which suggests damage of hollow spheres and accompanying alternations to the microstructural features. Interestingly, samples that showed a reduced storage modulus after exposure to high pressure and temperature conditions in liquid, also resulted in substantial uptake of weight. The increase in weight results from uptake of surrounding liquid into samples, indicating that constituents adjacent to the syntactic foams enter voids created by broken spheres and newly formed voids.

Controllable loss of mechanical integrity to repurpose syntactic foams as on-demand receptacles to retain constituents in the surrounding environment, resulting from externally triggered pressures and temperatures are detailed herein. Using solutions of Cr(III) and rhodamine-B as model analytes, our studies showed that this metal and this dye were captured within the syntactic foams, when the sample was exposed to pressures greater than isostatic crush strength of the hollow glass sphere and temperatures above the Tg of the polymer matrix. Moreover, saturation of samples with Cr(III) solutions occurs in a concentration dependent manner, wherein changing the concentration of Cr(III) solutions that surround the syntactic foams samples by an order of magnitude results in an accompanying order of magnitude change in the quantity of Cr(III) absorbed into the samples. This concept may be employed in new applications including environmental-dependent sampling and warrants continued advancement of syntactic foams to ensure materials properties match the tailored end use.

TABLE 1

Properties of Syntactic Foam Samples*

| Sample Name | Isostatic crush strength of spheres (psi) | Diameter of spheres (μm) | Sample density (g/mL) |
|---|---|---|---|
| ES-300 | 300 | 55 | 0.56 |
| ES-3K | 3,000 | 40 | 0.69 |
| ES-10K | 10,000 | 30 | 0.81 |
| ES-0 | NA | NA | 1.15 |

*Isostatic crush strength (target fractional survival at 90%) and diameter (particle size by volume, 50% distribution) provided from the manufacturer of microspheres

TABLE 2

Mechanical Properties of Samples without Environmental Exposures

| Sample Name | Storage Modulus at 35° C. (MPa) | Storage Modulus at 120° C. (MPa) | tan δ at 35° C. (×10$^{-3}$) | Maximum tan δ (×10$^{-3}$) | Temp (° C.) at peak tan |
|---|---|---|---|---|---|
| ES-0 | 2745 (±131) | 21 (±1) | 30 (±1) | 893 (±17) | 78 (±1) |
| ES-300 | 1847 (±18) | 132 (±6) | 19 (±1) | 384 (±15) | 80 (±0.4) |
| ES-3K | 2874 (±57) | 164 (±7) | 16 (±1) | 414 (±18) | 81 (±2) |
| ES-10K | 3780 (±15) | 189 (±2) | 16 (±1) | 445 (±7) | 81 (±1) |

TABLE 3

Properties of Samples After Exposure to Designated Pressure and Temperature*

| Sample Name | Applied Pressure (psi) | Applied Temp. (° C.) | Storage Modulus at 35° C. (MPa) | Storage Modulus at 120° C. (MPa) | tan δ at 35° C. (X 10$^{-3}$) | Maximum tan δ (X 10$^{-3}$) | Temp. (° C.) at maximum tan δ |
|---|---|---|---|---|---|---|---|
| ES-0 | NA** | NA | 2745 (±131) | 21 (±1) | 30 (±1) | 893 (±17) | 78 (±1) |
|  | 0 | 100 | 2684 (±84) | 20 (±0.5) | 29 (±0.4) | 570 (±16) | 74 (±0.3) |
|  | 1500 | 100 | 2731 (±65) | 21 (±1) | 27 (±2) | 617 (±64) | 77 (±3) |
|  | 7000 | 100 | 2711 (±43) | 21 (±0.3) | 28 (±1) | 630 (±26) | 78 (±1) |
|  | 7000 | 35 | 2782 (±67) | 20 (±0.3) | 27 (±0.1) | 805 (±5) | 78 (±0.2) |
|  | 15,000 | 100 | 2740 (±21) | 22 (±1) | 28 (±0.1) | 725 (±27) | 82 (±0.4) |
| ES-300 | NA | NA | 1847 (±18) | 132 (±6) | 19 (±1) | 384 (±15) | 80 (±0.4) |
|  | 0 | 100 | 1825 (±9) | 125 (±2) | 17 (±0.1) | 318 (±7) | 76 (±0.3) |
|  | 1500 | 100 | 977 (±30) | 17 (±2) | 51 (±2) | 420 (±4) | 73 (±1) |
|  | 7000 | 100 | 1299 (±30) | 31 (±4) | 42 (±3) | 374 (±5) | 76 (±1) |
|  | 7000 | 35 | 1614 (±14) | 33 (±3) | 27 (±1) | 335 (±7) | 71 (±1) |
|  | 15,000 | 100 | 1101 (±46) | 23 (±1) | 57 (±1) | 402 (±5) | 73 (±1) |
| ES-3K | NA | NA | 2874 (±57) | 164 (±7) | 16 (±1) | 414 (±18) | 81 (±2) |
|  | 0 | 100 | 2808 (±19) | 151(±4) | 17 (±0.3) | 365 (±7) | 78 (±0.3) |
|  | 1500 | 100 | 2865 (±52) | 163 (±4) | 18 (±0.3) | 375 (±11) | 80 (±1) |
|  | 7000 | 100 | 1795 (±29) | 42 (±3) | 35 (±1) | 374 (±18) | 73 (±1) |
|  | 7000 | 35 | 3018 (±60) | 174 (±5) | 14 (±0.3) | 417 (±5) | 81 (±0.2) |
|  | 15,000 | 100 | 1562 (±68) | 34 (±1) | 43 (±1) | 418 (±23) | 74 (±1) |
| ES-10K | NA | NA | 3780 (±15) | 189 (±2) | 16 (±1) | 445 (±7) | 81 (±1) |
|  | 0 | 100 | 3739 (±33) | 179 (±3) | 16 (±0.2) | 393 (±4) | 79 (±0.2) |
|  | 1500 | 100 | 3767 (±98) | 184 (±7) | 16 (±1) | 393 (±3) | 82 (±0.5) |
|  | 7000 | 100 | 3636 (±65) | 160 (±2) | 16 (±0.3) | 397 (±2) | 80 (±1) |
|  | 7000 | 35 | 3880 (±63) | 195 (±6) | 15 (±1) | 442 (±17) | 82 (±0.2) |
|  | 15,000 | 100 | 2448 (±73) | 57 (±1) | 31 (±1) | 399 (±3) | 77 (±1) |

*Samples were exposed to 8 wt % CaCl$_2$, 2 wt % NaCl for two hours at indicated temperature and pressure.
**NA are for samples without exposure to applied pressure, temperature, and moisture

REFERENCES

[1] N. Gupta, S.E. Zeltmann, V.C. Shunmugasamy, D. Pinisetty, Applications of Polymer Matrix Syntactic Foams, JOM 66(2) (2014) 245-254.

[2] J. Ben C. Gerwick, Construction in the Deep Sea, Third Edition ed., CRC Press, 2007.

[3] N.D. Gallo, C. James, H. Kevin, F. Patricia, H.B. Douglas, A.L. Lisa, Submersible- and lander-observed community patterns in the Mariana and New Britain trenches: Influence of productivity and depth on epibenthic and scavenging communities, Deep Sea Research Part I: Oceanographic Research Papers 99(Supplement C) (2015) 119-133.

[4] L. Watkins, E. Hershey, Syntactic foam improves deepwater flowline thermal insulation, Oil & Gas Journal, PennWell Corporation, Tulsa, 2001, pp. 49-54.

[5] X. Lefebvre, Sauvant-Moynot, D. Choqueuse, P. Chauchot, Durability of Syntactic Foams for Deep Offshore Insulation: Modelling of Water Uptake under Representative Ageing Conditions in Order to Predict the Evolution of Buoyancy and Thermal Conductivity, Oil & Gas Science and Technology—Rev. IFP 64(2) (2009) 165-178.

[6] A.J. Hodge, Kaul, R.K., McMahon, W.M., Sandwich Composite, Syntactic Foam Core Based, Application for Space Structures, 45th SAMPE' Symposium, Long Beach, CA; United States, 2000.

[7] A. Marshall, Sandwich Construction, in: G. Lubin (Ed.), Handbook of Composites, Springer US1982, p. 575.

[8] B. John, Reghunadhan Nair, C.P., Syntactic Foams, in: S.H. Goodman, Dodiuk-Kenig, H. (Ed.), Handbook of Thermoset Plastics, Elsevier, 2014.

[9] Advanced Materials: Adhesives, syntactics and laminating solutions for high performance, Huntsman Corporation, 2012.

[10] Handbook of Composite Reinforcements, in: S.M. Lee (Ed.) Wiley-VCH, 1993.

[11] P.K. Rohatgi, D. Weiss, N. Gupta, Applications of fly ash in synthesizing low-cost MMCs for automotive and other applications, JOM 58(11) (2006) 71-76.

[12] N. Gupta, D. Pinisetty, V.C. Shunmugasamy, Introduction, in: N. Gupta, D. Pinisetty, V.C. Shunmugasamy (Eds.), Reinforced Polymer Matrix Syntactic Foams: Effect of Nano and Micro-Scale Reinforcement, Springer International Publishing, Cham, 2013, pp. 1-8.

[13] F.A. Shutov, Syntactic polymer foams, Chromatography/Foams/Copolymers, Springer Berlin Heidelberg, Berlin, Heidelberg, 1986, pp. 63-123.

[14] L. Zhang, J. Ma, Effect of coupling agent on mechanical properties of hollow carbon microsphere/phenolic resin syntactic foam, Composites Science and Technology 70(8) (2010) 1265-1271.

[15] S.T. Benton, C.R. Schmitt, Preparation of syntactic carbon foam, Carbon 10(2) (1972) 185-190.

[16] N. Gupta, R. Ye, M. Porfiri, Comparison of tensile and compressive characteristics of vinyl ester/glass microballoon syntactic foams, Composites Part B: Engineering 41(3) (2010) 236-245.

[17] C. Swetha, R. Kumar, Quasi-static uni-axial compression behaviour of hollow glass microspheres/epoxy based syntactic foams, Materials & Design 32(8) (2011) 4152-4163.

[18] X.F. Tao, L.P. Zhang, Y.Y. Zhao, Al matrix syntactic foam fabricated with bimodal ceramic microspheres, Materials & Design 30(7) (2009) 2732-2736.

[19] D.K. Balch, D.C. Dunand, Load partitioning in aluminum syntactic foams containing ceramic microspheres, Acta Materialia 54(6) (2006) 1501-1511.

[20] G. Nikhil, N. Ruslan, Tensile properties of glass microballoon-epoxy resin syntactic foams, Journal of Applied Polymer Science 102(2) (2006) 1254-1261.

[21] B. Song, W. Chen, D.J. Frew, Dynamic Compressive Response and Failure Behavior of an Epoxy Syntactic Foam, Journal of Composite Materials 38(11) (2004) 915-936.

[22] K. Okuno, R.T. Woodhams, Mechanical Properties and Characterization of Phenolic Resin Syntactic Foams, Journal of Cellular Plastics 10(5) (1974) 237-244.

[23] D.U. Shah, F. Vollrath, D. Porter, Silk cocoons as natural macro-balloon fillers in novel polyurethane-based syntactic foams, Polymer 56 (2015) 93-101.

[24] M. Koopman, K.K. Chawla, K.B. Carlisle, G.M. Gladysz, Microstructural failure modes in three-phase glass syntactic foams, J Mater Sci 41(13) (2006) 4009-4014.

[25] B. John, C.P.R. Nair, K.A. Devi, K.N. Ninan, Effect of low-density filler on mechanical properties of syntactic foams of cyanate ester, J Mater Sci 42(14) (2007) 5398-5405.

[26] H.S. Kim, P. Plubrai, Manufacturing and failure mechanisms of syntactic foam under compression*, Composites Part A: Applied Science and Manufacturing 35(9) (2004) 1009-1015.

[27] L. Bardella, G. Perini, A. Panteghini, N. Tessier, N. Gupta, M. Porfiri, Failure of glass-microballoons/thermoset-matrix syntactic foams subject to hydrostatic loading, European Journal of Mechanics—A/Solids 70 (2018) 58-74.

[28] N. Gupta, E. Woldesenbet, P. Mensah, Compression properties of syntactic foams: effect of cenosphere radius ratio and specimen aspect ratio, Composites Part A: Applied Science and Manufacturing 35(1) (2004) 103-111.

[29] E. Rizzi, E. Papa, A. Corigliano, Mechanical behavior of a syntactic foam: experiments and modeling, International Journal of Solids and Structures 37(40) (2000) 5773-5794.

[30] L. Bardella, F. Malanca, P. Ponzo, A. Panteghini, M. Porfiri, A micromechanical model for quasi-brittle compressive failure of glass-microballoons/thermoset-matrix syntactic foams, Journal of the European Ceramic Society 34(11) (2014) 2605-2616.

[31] N. Gupta, E. Woldesenbet, Hygrothermal studies on syntactic foams and compressive strength determination, Composite Structures 61(4) (2003) 311-320.

[32] R.L. Poveda, G. Dorogokupets, N. Gupta, Carbon nanofiber reinforced syntactic foams: Degradation mechanism for long term moisture exposure and residual compressive properties, Polymer Degradation and Stability 98(10) (2013) 2041-2053.

[33] C.S. Karthikeyan, S. Sankaran, Effect of Absorption in Aqueous and Hygrothermal Media on the Compressive Properties of Glass Fiber Reinforced Syntactic Foam, Journal of Reinforced Plastics and Composites 20(11) (2001) 982-993.

[34] V. Sauvant-Moynot, N. Gimenez, H. Sautereau, Hydrolytic ageing of syntactic foams for thermal insulation in deep water: degradation mechanisms and water uptake model, J Mater Sci 41(13) (2006) 4047-4054.

[35] V. Sauvant-Moynot, S. Duval, N. Gimenez, J. Kittel, Hot wet aging of glass syntactic foam coatings monitored by impedance spectroscopy, Progress in Organic Coatings 59(3) (2007) 179-185.

[36] F. Grosjean, N. Bouchonneau, D. Choqueuse, V. Sauvant-Moynot, Comprehensive analyses of syntactic foam behaviour in deepwater environment, J Mater Sci 44(6) (2009) 1462-1468.

[37] V. Sauvant-Moynot, Gimenez, N., Adrien, J., Maire, E., X-Ray Microtomography for a Better Understanding of Syntactic Foam Performance and Limits in Ultra Deep Water, Oilfield Engineering with Polymers 2006, London, England, 2006, p. 7.

[38] N. Gimenez, V.r. Sauvant-Moynot, H. Sautereau, Wet Ageing of Syntactic Foams Under High Pressure/High Temperature in Deionized Water, (41979) (2005) 205-210.

[39] J. Lachambre, E. Maire, J. Adrien, D. Choqueuse, In situ observation of syntactic foams under hydrostatic pressure using X-ray tomography, Acta Materialia 61(11) (2013) 4035-4043.

[40] J.J.A. DeRuntz, 0. Hoffman, The Static Strength of Syntactic Foams, Journal of Applied Mechanics 36(3) (1969) 551-557.

[41] P. Viot, Hydrostatic compression on polypropylene foam, International Journal of Impact Engineering 36(7) (2009) 975-989.

[42] O. Wurl, J.P. Obbard, Distribution of organochlorine compounds in the sea-surface microlayer, water column and sediment of Singapore's coastal environment, Chemosphere 62(7) (2006) 1105-1115.

[43] V. Tornero, G. Hanke, Chemical contaminants entering the marine environment from sea-based sources: A review with a focus on European seas, Marine Pollution Bulletin 112(1) (2016) 17-38.

[44] V. Shunmugasamy, D. Pinisetty, N. Gupta, Viscoelastic properties of hollow glass particle filled vinyl ester matrix syntactic foams: effect of temperature and loading frequency, J Mater Sci 48(4) (2013) 1685-1701.

[45] G. Tagliavia, M. Porfiri, N. Gupta, Vinyl Ester—Glass Hollow Particle Composites: Dynamic Mechanical Properties at High Inclusion Volume Fraction, Journal of Composite Materials 43(5) (2009) 561-582.

[46] D. Romanzini, A. Lavoratti, H.L. Ornaghi Jr, S.C. Amico, A.J. Zattera, Influence of fiber content on the mechanical and dynamic mechanical properties of glass/ramie polymer composites, Materials & Design 47(0) (2013) 9-15.

[47] A. Kadkhoda Ghamsari, E. Zegeye, E. Woldesenbet, Viscoelastic properties of syntactic foam reinforced with short sisal fibers, Journal of Composite Materials (2013).

[48] B. John, R. Nair, Update on Syntactic Foams, 2010.

[49] S.C. George, S. Thomas, Transport phenomena through polymeric systems, Progress in Polymer Science 26(6) (2001) 985-1017.

[50] R. Rubio, A. Sahuquillo, G. Rauret, P. Quevauviller, Determination of Chromium in Environmental and Biological Samples by Atomic Absorption Spectroscopy: A Review, International Journal of Environmental Analytical Chemistry 47(2) (1992) 99-128.

[51] R.J. Vitale, G.R. Mussoline, K.A. Rinehimer, Environmental Monitoring of Chromium in Air, Soil, and Water, Regulatory Toxicology and Pharmacology 26(1) (1997) S80-S85.

That which is claimed:

1. An environmental constituent collecting vehicle comprising a syntactic foam, the syntactic foam comprising: a polymer matrix; and hollow microspheres, wherein the polymer matrix is prepared from an epoxy resin formulation comprising a diglycidyl ether of bisphenol A or bisphenol F, butyl glycidyl ether, and triethylene tetraamine (TETA).

2. The environmental constituent collecting vehicle of claim 1, wherein the hollow microspheres comprise between 30 and 60 volume percent of the syntactic foam.

3. The environmental constituent collecting vehicle of claim 1, wherein the hollow microspheres comprise glass microspheres.

4. The environmental constituent collecting vehicle of claim 3, wherein the glass microspheres have a crush strength in a range of 250 psi to 28,000 psi.

5. The environmental constituent collecting vehicle of claim 1, wherein the epoxy resin formulation comprises the diglycidyl ether of bisphenol A.

6. The environmental constituent collecting vehicle of claim 1, wherein the syntactic foam has a glass transition temperature in a range of 70° C. to 85° C.

7. A method of collecting and analyzing an environmental constituent comprising: providing a vehicle for collecting the environmental constituent comprising a syntactic foam to an environment, the syntactic foam comprising a polymer matrix and hollow microspheres; collecting the environmental constituent from the environment with the vehicle; and analyzing the environmental constituent, wherein the polymer matrix is prepared from an epoxy resin formulation comprising a diglycidyl ether of bisphenol A or bisphenol F, butyl glycidyl ether, and triethylene tetraamine (TETA), and wherein collecting of the environmental constituent is initiated by pressure and/or temperature in the environment, and wherein pressure in the environment at which the environmental constituent is collected exceeds a crush strength of the hollow microspheres, and/or wherein temperature in the environment at which the environmental constituent is collected exceeds a glass transition temperature of the syntactic foam.

8. The method of claim 7, wherein the hollow microspheres comprise between 30 and 60 volume percent of the syntactic foam.

9. The method of claim 7, wherein the hollow microspheres comprise glass microspheres.

10. The method of claim 9, wherein the glass microspheres have a crush strength in a range of 250 psi to 28,000 psi.

11. The method of claim 7, wherein the epoxy resin formulation comprises the diglycidyl ether of bisphenol A.

12. The method of claim 7, wherein the syntactic foam has a glass transition temperature in a range of 70° C. to 85° C.

13. The method of claim 7, wherein the environment is a deep-sea marine environment.

14. The method of claim 7, wherein the environment comprises an oil or gas well pipeline, and the environmental constituent is collected from the oil or gas well pipeline.

15. The method of claim 7, wherein the environment is a marine water environment, and the environmental constituent collected is analyzed for impurities or pollutants to monitor quality of marine water.

16. The method of claim 7, wherein the environmental constituent collected is analyzed for metal contamination to determine if metal contamination is present in the environment.

17. A method of collecting and analyzing a sample from an oil or gas well or pipeline comprising:

providing a vehicle for collecting the sample comprising a syntactic foam to the oil or gas well or pipeline, the syntactic foam comprising a polymer matrix and hollow microspheres;

collecting the sample from the oil or gas well or pipeline with the vehicle; and analyzing the sample collected from the oil or gas well or pipeline, wherein the polymer matrix is prepared from an epoxy resin formulation comprising a diglycidyl ether of bisphenol A or bisphenol F, butyl glycidyl ether, and triethylene tetraamine (TETA), and wherein collecting of the sample is initiated by pressure and/or temperature in the oil or gas well or pipeline, and wherein pressure at which the sample is collected exceeds a crush strength of the hollow microspheres, and/or wherein temperature at which the sample is collected exceeds a glass transition temperature of the syntactic foam.

18. The method of claim 17, wherein the epoxy resin formulation comprises the diglycidyl ether of bisphenol A.

* * * * *